(12) United States Patent
Schoonmaker

(10) Patent No.: US 9,731,081 B2
(45) Date of Patent: Aug. 15, 2017

(54) CONTACT TRIGGER RELEASE NEEDLE GUARD WITH ELASTIC SPRING

(71) Applicant: SAFETY SYRINGES, INC., Carlsbad, CA (US)

(72) Inventor: Ryan Schoonmaker, San Marcos, CA (US)

(73) Assignee: SAFETY SYRINGES, INC., Carlsbad, CA (US)

( * ) Notice: Subject to any disclaimer, the term of this patent is extended or adjusted under 35 U.S.C. 154(b) by 170 days.

(21) Appl. No.: 14/877,659

(22) Filed: Oct. 7, 2015

(65) Prior Publication Data

US 2016/0175538 A1     Jun. 23, 2016

Related U.S. Application Data

(63) Continuation of application No. 13/802,130, filed on Mar. 13, 2013, now Pat. No. 9,278,179.

(60) Provisional application No. 61/662,303, filed on Jun. 20, 2012.

(51) Int. Cl.
*A61M 5/32*     (2006.01)

(52) U.S. Cl.
CPC ........ *A61M 5/3243* (2013.01); *A61M 5/3202* (2013.01); *A61M 5/3204* (2013.01); *A61M 5/326* (2013.01); *A61M 5/3271* (2013.01); *A61M 5/3272* (2013.01); *A61M 2005/3258* (2013.01); *A61M 2005/3267* (2013.01); *A61M 2205/19* (2013.01); *A61M 2205/581* (2013.01); *A61M 2205/586* (2013.01)

(58) Field of Classification Search
CPC .. A61M 2005/3258; A61M 2005/3267; A61M 5/3202; A61M 5/3204; A61M 5/326; A61M 5/3271; A61M 5/3272
See application file for complete search history.

(56) References Cited

U.S. PATENT DOCUMENTS

| | | | |
|---|---|---|---|
| 6,575,939 B1 | 6/2003 | Brunel | |
| 2004/0039340 A1 | 2/2004 | Prais et al. | |
| 2007/0106225 A1 | 5/2007 | Millerd | |
| 2009/0326477 A1 | 12/2009 | Liversidge | |
| 2011/0319817 A1 | 12/2011 | Rubinstein et al. | |

FOREIGN PATENT DOCUMENTS

WO     WO 2008/127195     10/2008

OTHER PUBLICATIONS

WO PCT/US2013/046618 ISR, Nov. 14, 2013.
WO PCT/US2013/046618 IPRP, Dec. 23, 2014.

*Primary Examiner* — Rebecca E Eisenberg
(74) *Attorney, Agent, or Firm* — One LLP

(57) ABSTRACT

A needle guard device mountable to a pre-filled syringe in its ready-to-fill state. The device includes a device shield interconnected to a lock collar with flexible member and biased to move relative to the lock collar. The lock collar interfaces with the syringe neck to attach the device to the syringe. As the device shield moves proximally, rotation arms of the lock collar interact with angled cutouts in the device shield, causing the device shield to rotate relative to the lock collar and disengaging one or more keys on the device shield from one or more keyways in the lock collar triggering the device shield to move from a first configuration in which the device shield is retractable to expose a syringe sharp to a second configuration in which the device shield is fixedly positioned to cover the syringe sharp.

20 Claims, 38 Drawing Sheets

CONTACT TRIGGER RELEASE NEEDLE GUARD WITH ELASTIC SPRING

CROSS-REFERENCE TO RELATED APPLICATIONS

This application is a continuation application of U.S. patent application Ser. No. 13/802,130, filed Mar. 13, 2013, which claims the benefit of U.S. Provisional Application No. 61/662,303, filed Jun. 20, 2012, both of which applications are incorporated herein by reference.

FIELD

The embodiments provided herein relate generally to safety systems for syringes, and more particularly to a needle guard for a syringe that includes an automatically activated shield for covering a needle of the syringe.

BACKGROUND INFORMATION

Medication is often dispensed using a medicine cartridge, such as a glass syringe, having a barrel with a needle at one end and a plunger slidably inserted into the other end and coupled to a rubber stopper. Such cartridges are often referred to as "pre-filled syringes" because they may contain a specific dosage or volume of medication when they are initially provided, as compared to conventional syringes that are furnished empty and filled by the user before making an injection.

The glass syringe and rubber stopper have, for years, provided an ideal drug storage closure having unique properties of impermeability to oxygen, low extractables, biocompability, durability, etc. However, they are both formed by processes that do not lend themselves to tight geometrical tolerances. Tight tolerances were not originally needed by these devices because they were not used mechanically with other devices.

Due to the risk of communicable diseases, a number of syringes and adapters have been developed that are intended to prevent accidental needle sticks and/or inadvertent reuse of a syringe. Conventional passive anti-needle stick safety devices for prefilled syringes must mount to the syringe but not interfere excessively with the force required to move the plunger rod during injection nor prevent the full travel of the plunger rod. The safety mechanism necessarily must be triggered toward the end of the administration of the drug or injection (i.e., near the end of the plunger rod travel). However, since virtually all safety devices locate the syringe against the safety device at a point under the syringe finger flange, the operability of the safety device tends to be dependent on the tolerances of the syringe and stopper.

In addition, because conventional passive anti-needle stick safety devices for prefilled syringes tend to mount to or on the barrel of the syringe, the safety devices tend to obscure the contents of the syringe and must be applied post filling of the syringe.

Prefilled syringes tend to be shipped to pharmaceutical customers as ready-to-fill syringes, which are syringes that have been thoroughly cleaned inside and outside after the forming processes and attachment of a needle have been completed, and then placed in sealed tubs that are then sterilized and shipped to the pharmaceutical customers ready for filling with a medicine. The syringe tubs may contain 100 to 160 syringes, each with a geometrical spacing and access that is consistent with established syringe handling equipment. A safety device applied to the syringe must not obscure the optical inspection systems that are in place to check the syringes prior to filling them with medication.

Accordingly, it would be desirable to have a needle guard for a ready-to-fill syringe having the safety device triggering mechanism independent of the syringe and stopper tolerances, and that assembles to the syringe without adversely affecting the syringe position with respect to the syringe handling tub or the way the handling equipment conveys the syringes during filling and packaging nor impedes the inspection processes.

SUMMARY

The systems and methods described herein are directed to a needle guard for a syringe having the safety device triggering mechanism independent of the syringe and stopper tolerances. A contact trigger release needle guard device described herein is an anti-needle stick device designed to be attached to the distal end of a ready-to-fill syringe. The needle guard device includes a lock collar and a device shield moveable relative to the lock collar. The device shield is biased relative to the lock collar by an elastic spring coupled between the device shield and the lock collar. The lock collar interfaces with a syringe neck and recess to attach the needle guard device to the ready-to-fill syringe. With the removal of a rigid needle shield subassembly comprising rigid and soft needle shield components, the device shield is free to move proximally along the syringe neck and interact with the lock collar triggering the device shield to move relative to the lock collar from a first configuration, where the device shield is moveable to expose a syringe sharp to a second configuration where the needle is fixedly shielded or covered.

In use, a device user removes the rigid needle shield subassembly, inserts the syringe sharp, such as a needle, into an injection site and pushes down on the syringe past the point of initial contact of the device shield with the skin, moving the device shield proximally along the lock collar. As the device shield moves proximally along the lock collar, rotation arms of the lock collar interact with angled cutouts in the device shield causing the device shield to rotate relative to the lock collar and disengage one or more keys on the device shield from one or more keyways in the lock collar, triggering the device shield to move from a first configuration where the device shield is retractable to expose a syringe sharp, to a second configuration where the device shield is fixedly positioned to shield or cover the syringe sharp.

Other systems, methods, features and advantages of the invention will be or will become apparent to one with skill in the art upon examination of the following figures and detailed description.

BRIEF DESCRIPTION OF THE FIGURES

The details of the invention, including fabrication, structure and operation, may be gleaned in part by study of the accompanying figures, in which like reference numerals refer to like parts. The components in the figures are not necessarily to scale, emphasis instead being placed upon illustrating the principles of the invention. Moreover, all illustrations are intended to convey concepts, where relative sizes, shapes and other detailed attributes may be illustrated schematically rather than literally or precisely.

DETAILED DESCRIPTION

Figure 1:
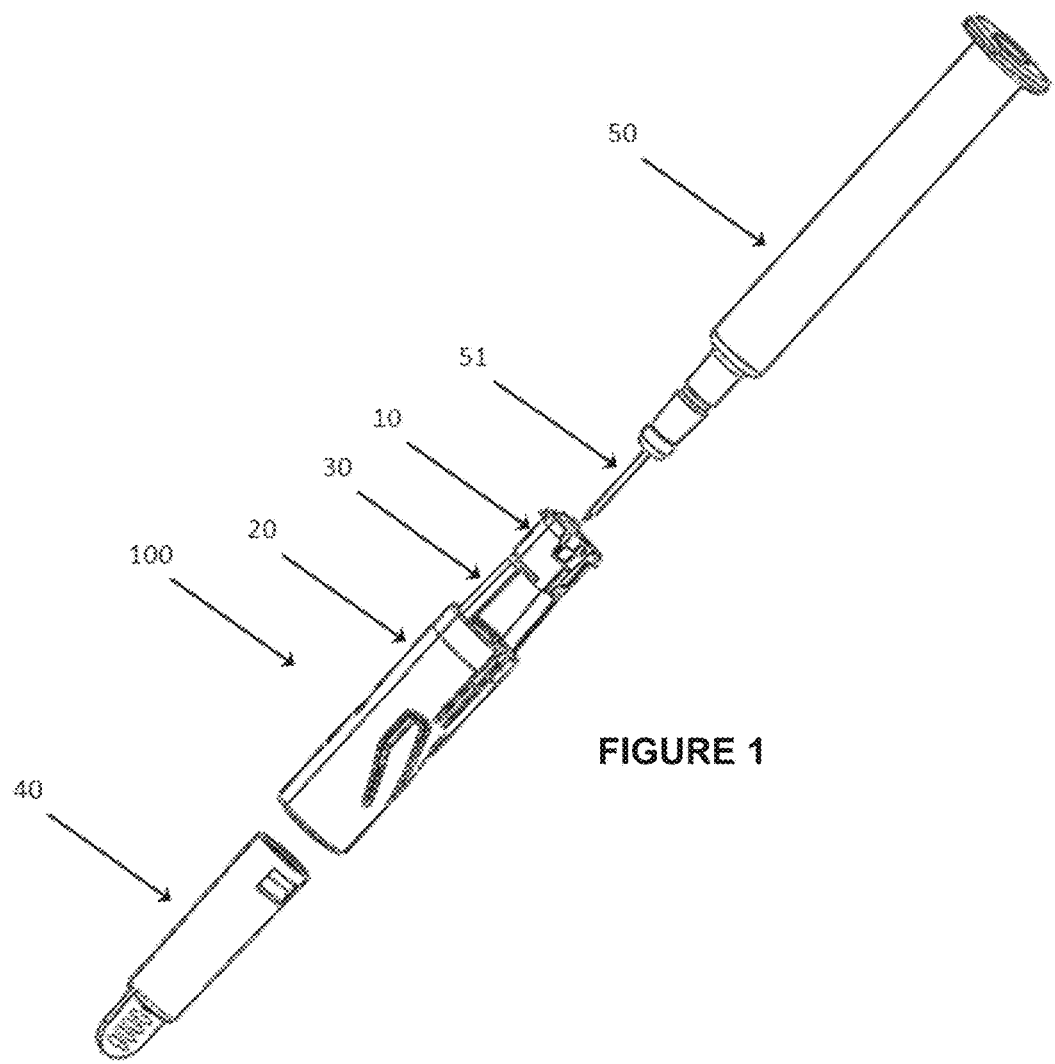
FIG. 1 is an isometric view of an exploded assembly of a safety device with a syringe.
Figure 2:
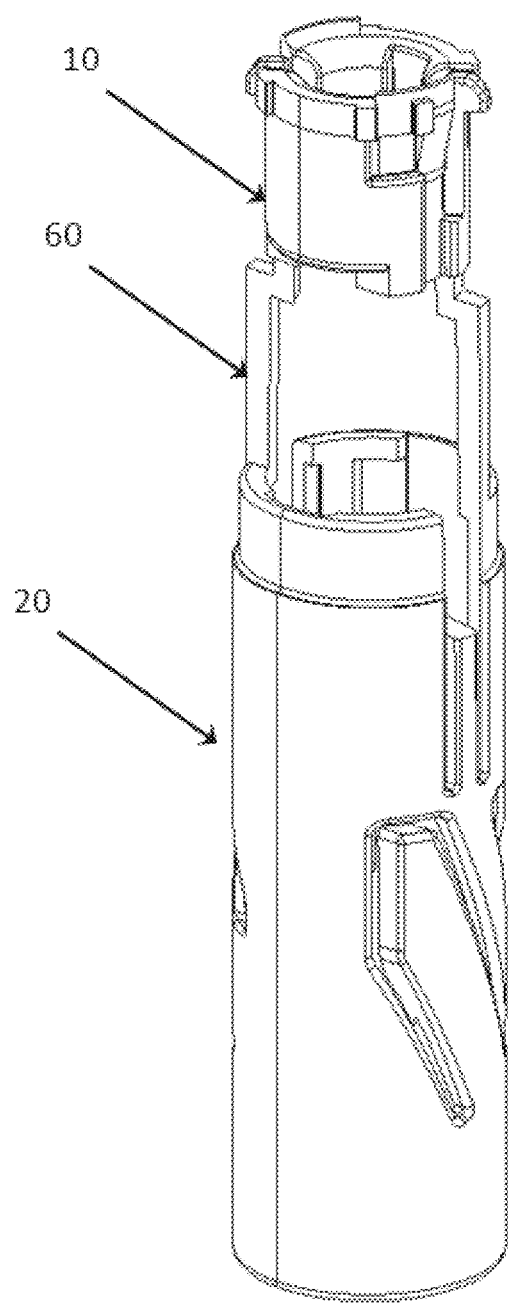
FIG. 2 is an isometric view of a lock collar and a device shield after a first step (polymer injection molding—1st shot) in a process of manufacturing the integrated lock collar, device shield, and flexible interconnect part.
Figure 3:
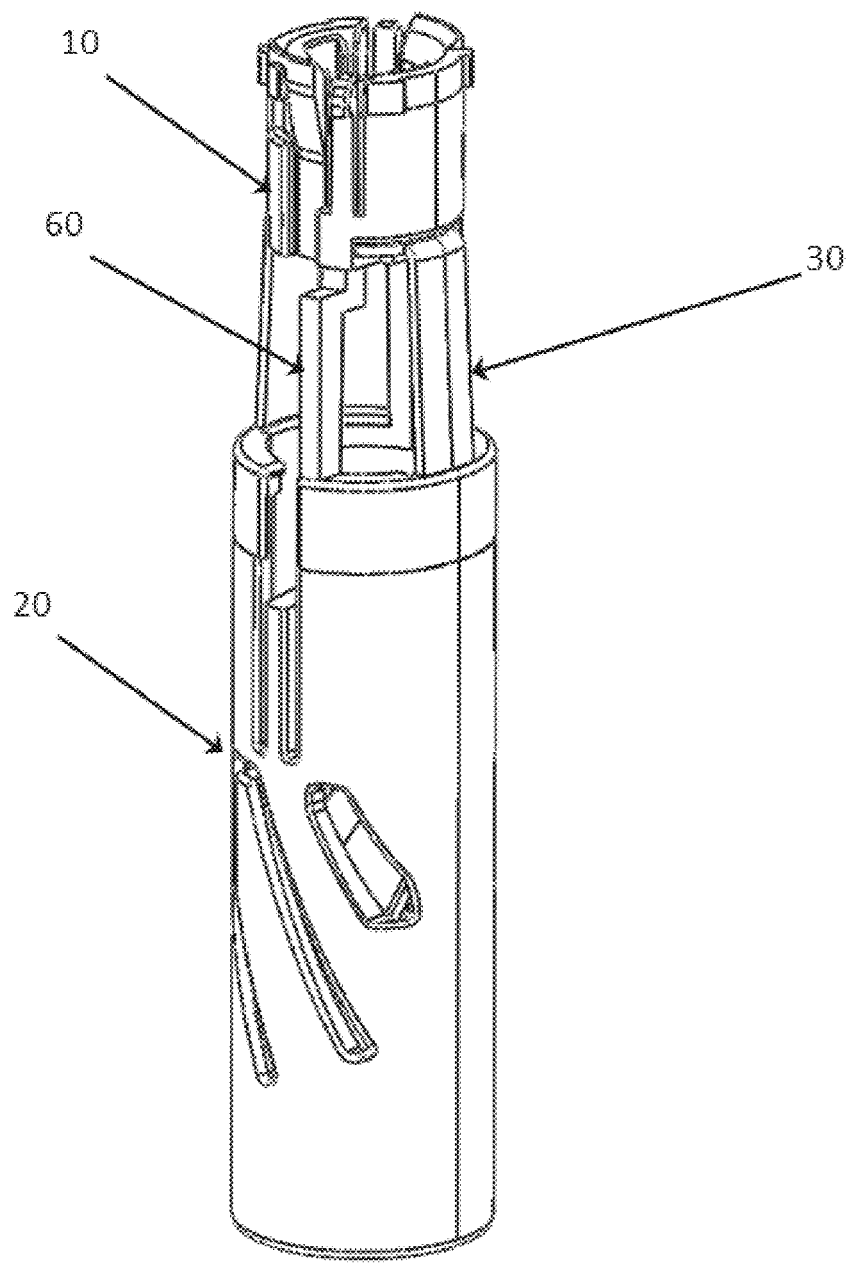
FIG. 3 is an isometric view of the lock collar, device shield, and flexible interconnect after a second step (TPE injection molding—2nd shot) in the process of manufacturing the integrated lock collar, device shield, and flexible interconnect part.
Figure 4:
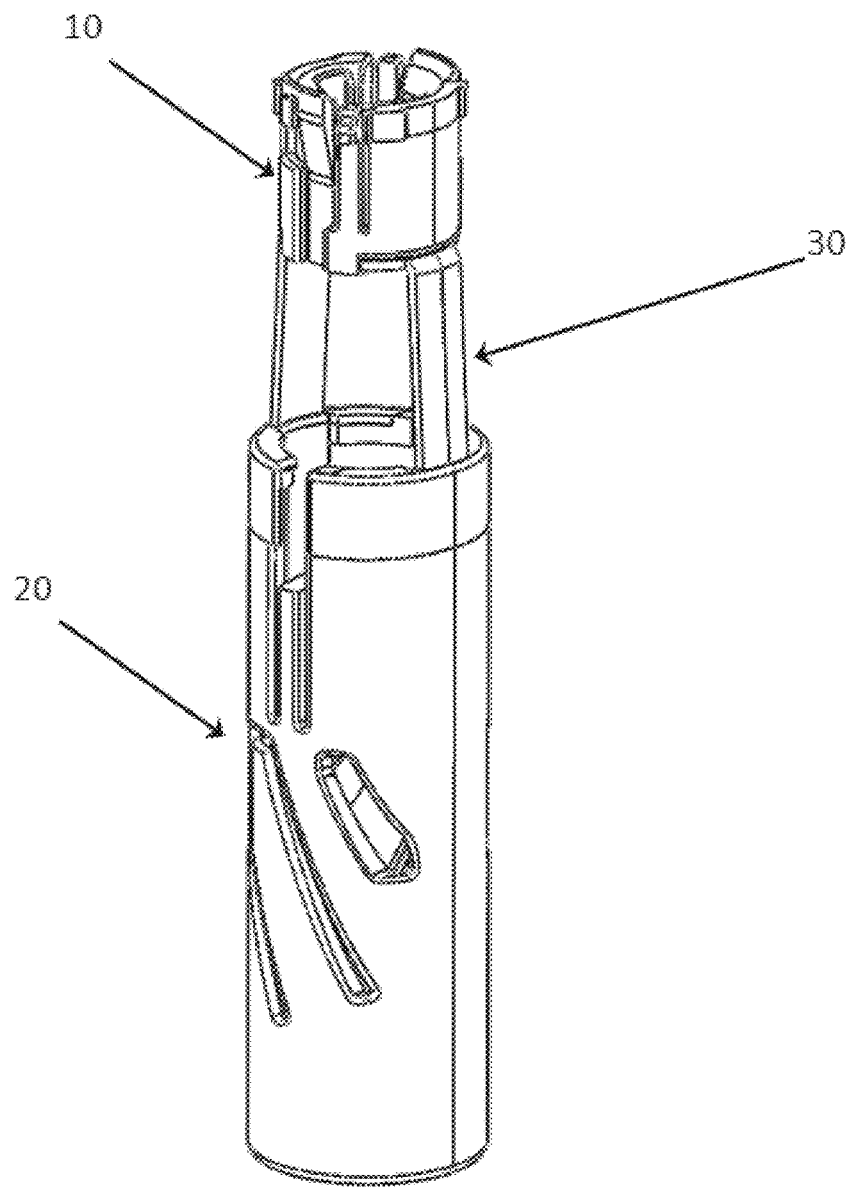
FIG. 4 is an isometric view of the lock collar, device shield, and flexible interconnect after a third step (clipping of the lock collar/device shield bridges) in the process of manufacturing the integrated lock collar, device shield, and flexible interconnect part.

The systems and methods described herein are directed to a needle guard for a syringe having the safety device triggering mechanism independent of the syringe geometry. Turning now to the figures, FIGS. 1-38 show embodiments of a contact trigger release needle guard. The needle guard described herein is an anti-needle stick safety device designed to be attached to the distal end of a prefilled syringe in its ready-to-fill state. As depicted in FIG. 1, an anti-needle stick safety device or needle guard 100 is designed to be attached to the distal end of a syringe 50 in its ready-to-fill state. The device 100 is comprised of a lock collar 10, a device shield 20, a flexible interconnect 30 and a rigid needle shield 40 comprised of a rigid outer component 41 and a soft inner component 42 (see, FIGS. 7, 9 & 10). In a preferred embodiment, the lock collar 10, device shield 20, and flexible interconnect 30 are produced in one injection molding process. The process consists of injection molding the lock collar 10 and device shield 20 in a first injection molding shot with a single polymer material. As depicted in FIG. 2, the two parts may be connected via a thin bridge 60 of material or via a runner system in what is typically known as a family mold. A second injection molding shot would consist of a flexible material such as a thermoplastic elastomer (TPE), which would produce a flexible interconnect 30 that physically connects the lock collar 10 to the device shield 20 as shown in FIG. 3. During the injection molding process the flexible interconnect 30 would physically bond to the lock collar 10 and device shield 20. Alternatively, the lock collar 10 and device shield 20 may be designed such that when the flexible interconnect 30 is injection molded, a physical mechanical bond is created between the parts. The last step in the process is to clip off the bridge 60. The safety device 100 is depicted in FIG. 4 without the bridge 60.

Figure 5:
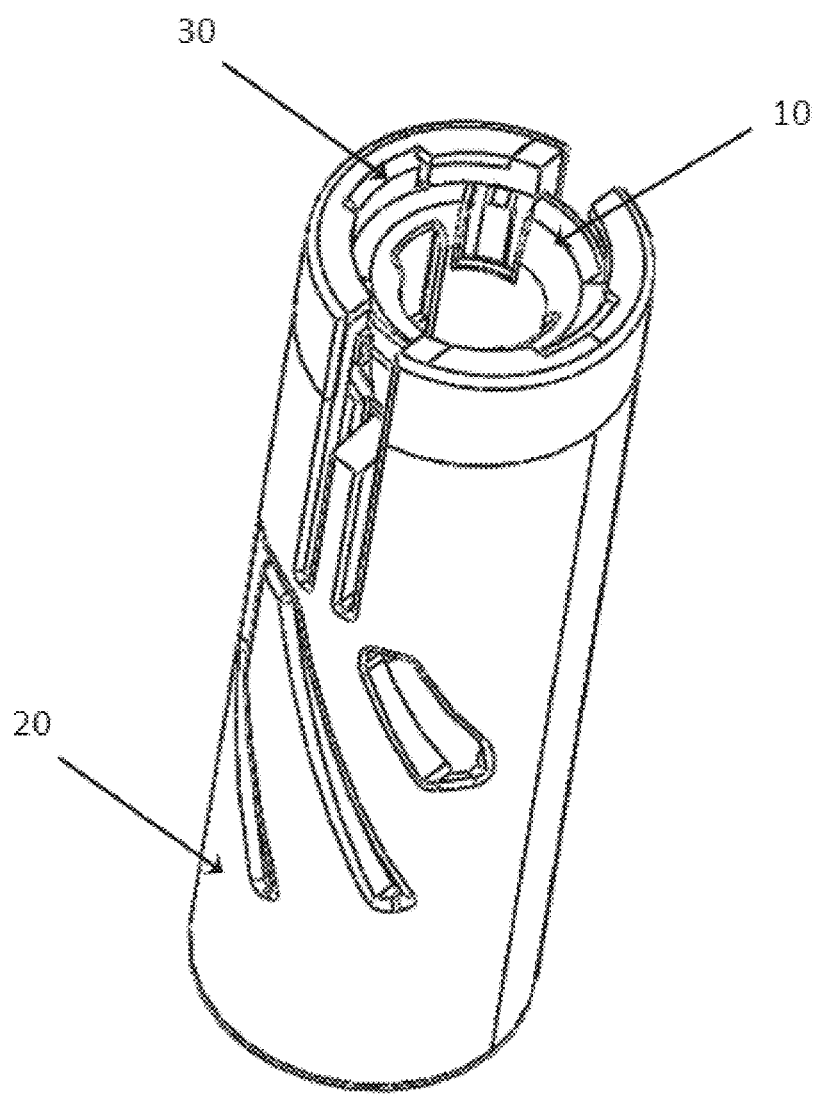
FIG. 5 is an isometric view of the integrated lock collar, device shield, and flexible interconnect part assembled together with the lock collar inserted into the device shield.
Figure 6:
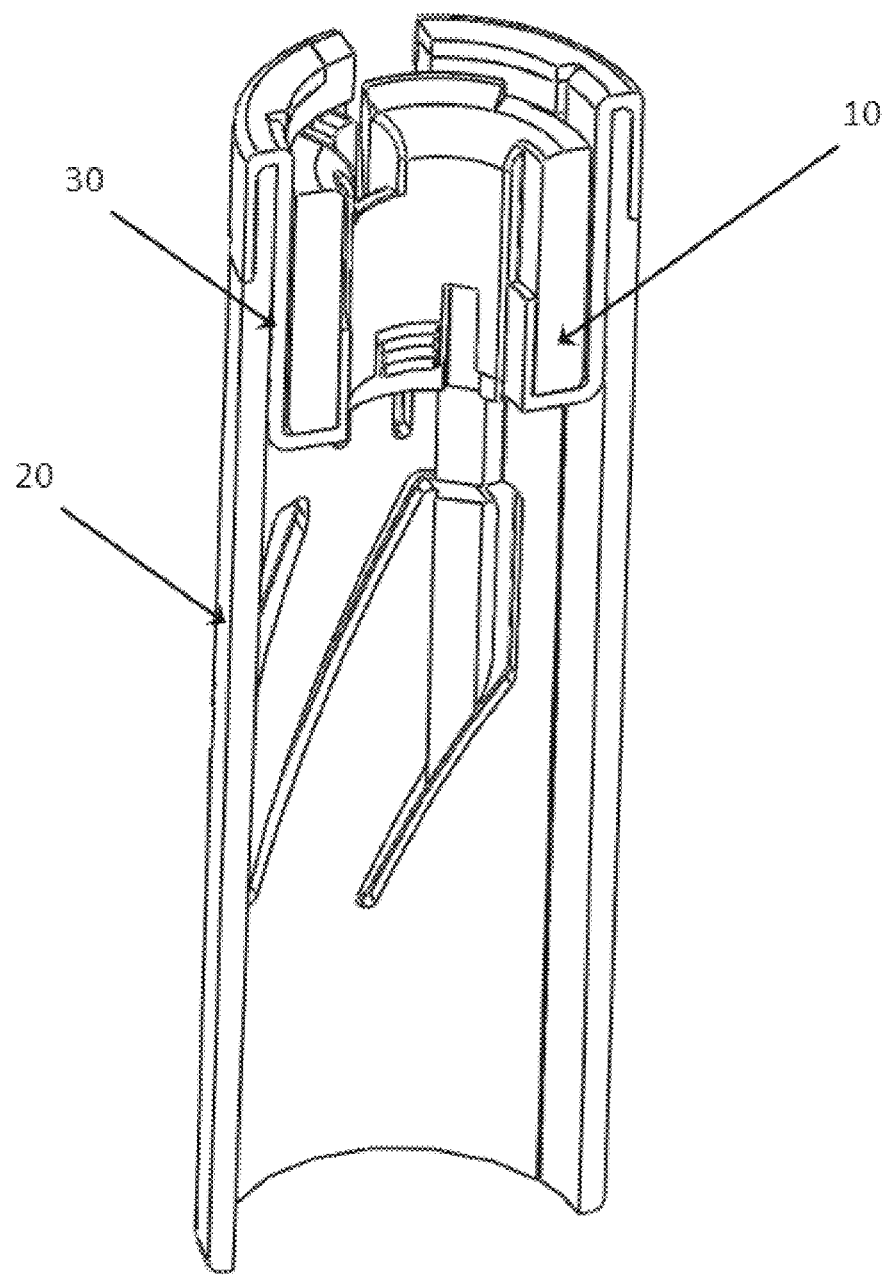
FIG. 6 is a cross sectional view of the integrated lock collar, device shield, and flexible interconnect part assembled together with the lock collar inserted into the device shield.

As shown in FIGS. 5 and 6, when the safety device 100 is assembled the lock collar 10 is pushed or inserted within the device shield 20. This step is made possible by the flexibility of the flexible interconnect 30, which is coupled to and positioned between the lock collar 10 and device shield 20.

Figure 7:
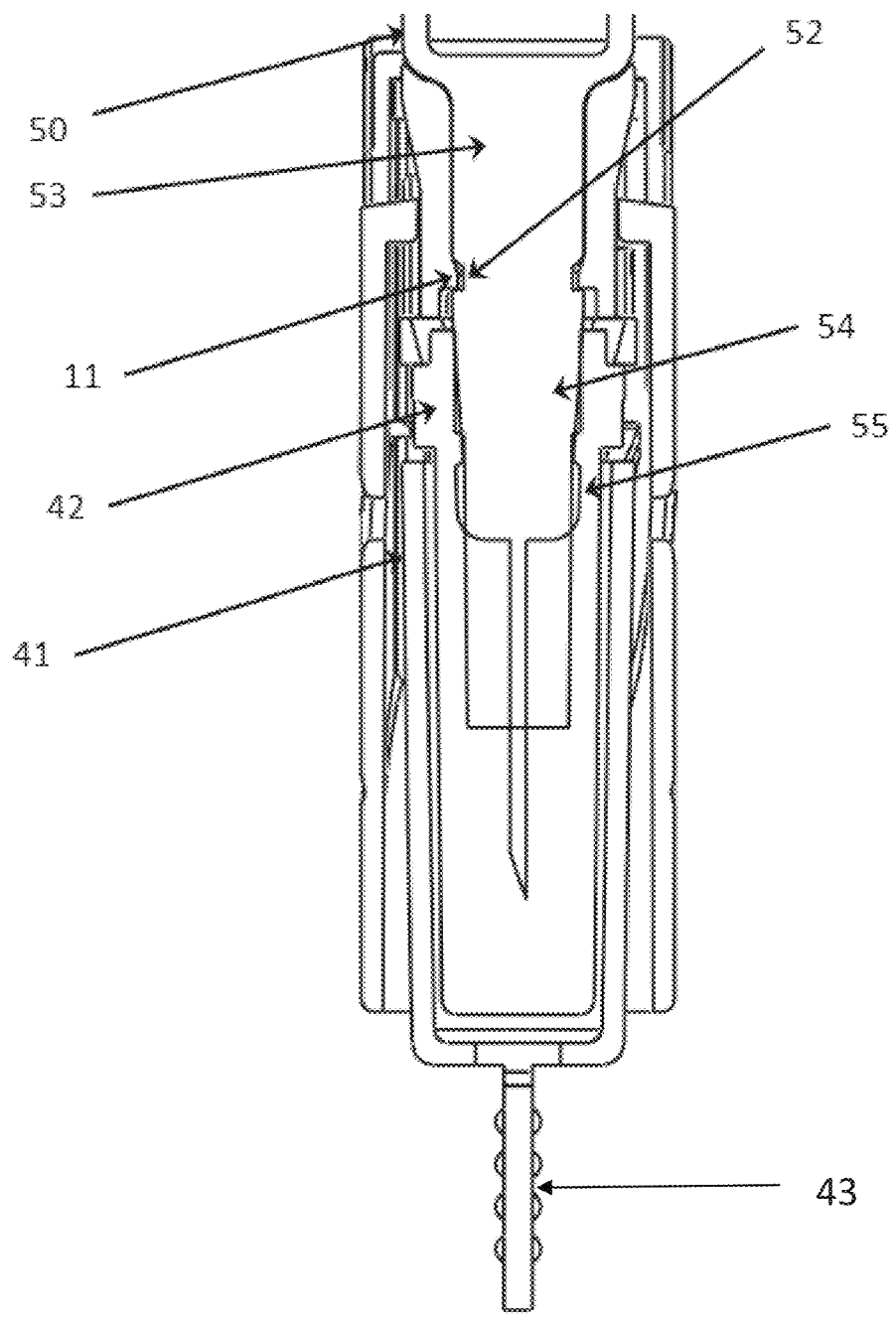
FIG. 7 is a cross sectional view of the safety device assembled to a syringe neck with a rigid needle shield (RNS) in place prior to use.
Figure 8:
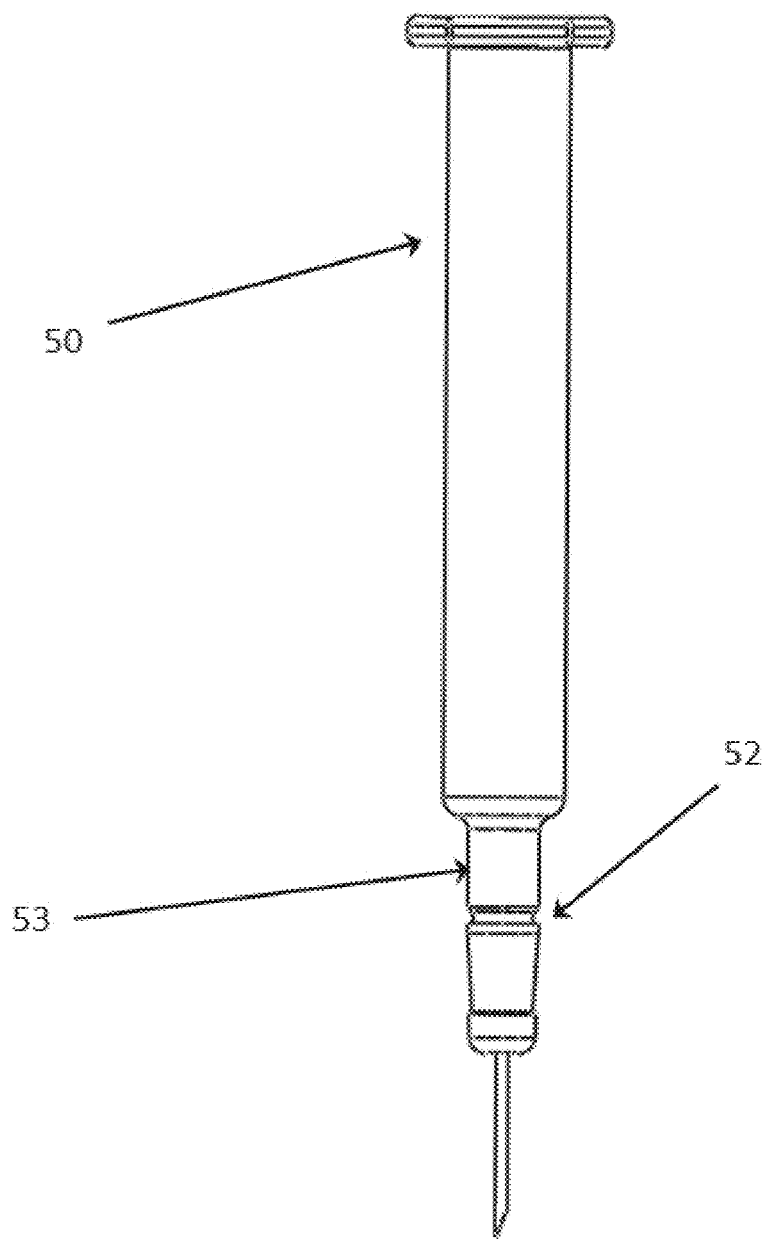
FIG. 8 is a front view of a syringe with a custom neck for integration with the safety device.
Figure 9:
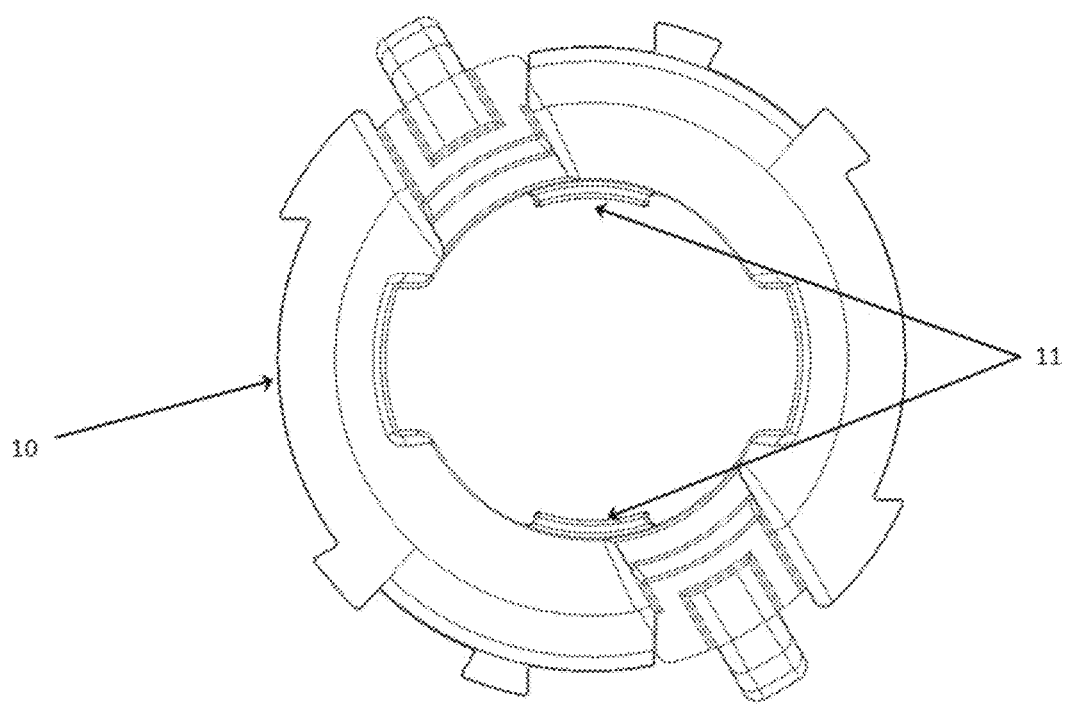
FIG. 9 is a top view of the lock collar of the safety device.
Figure 10:
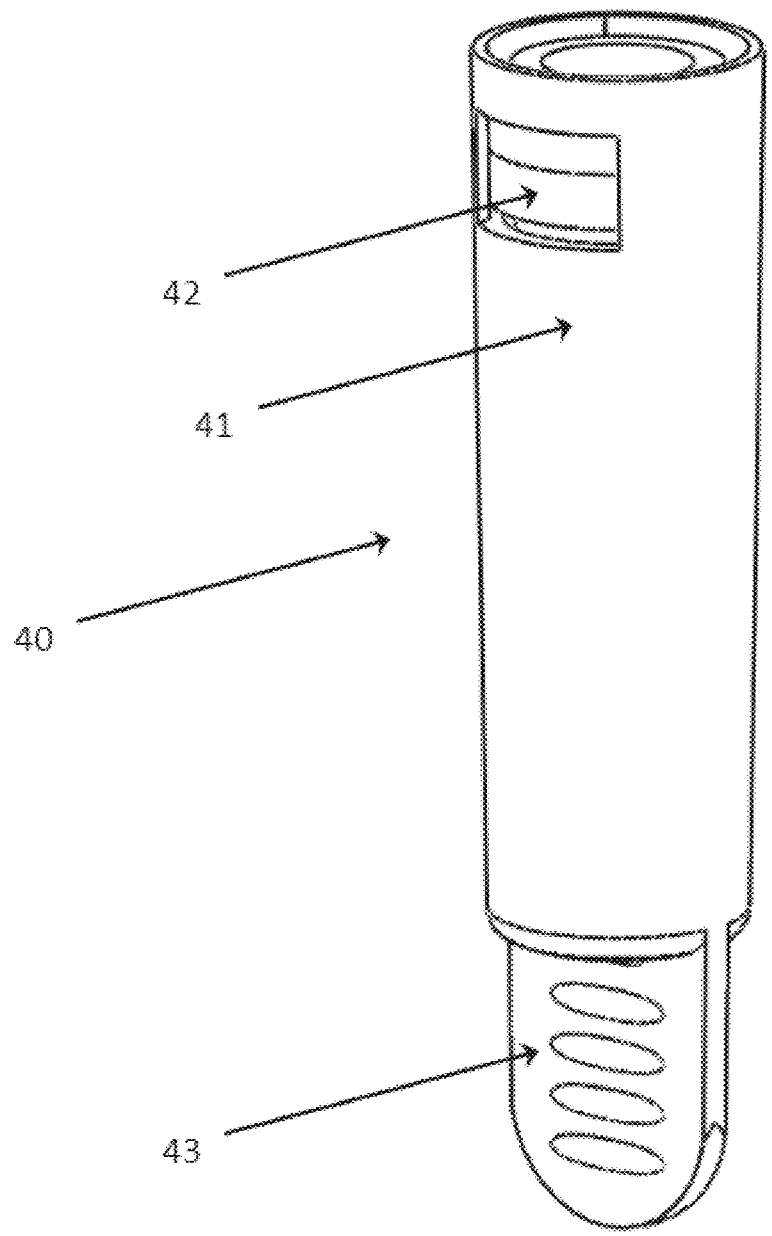
FIG. 10 is an isometric view of the RNS with an integrated grip for easy removal from the safety device.
Figure 11:
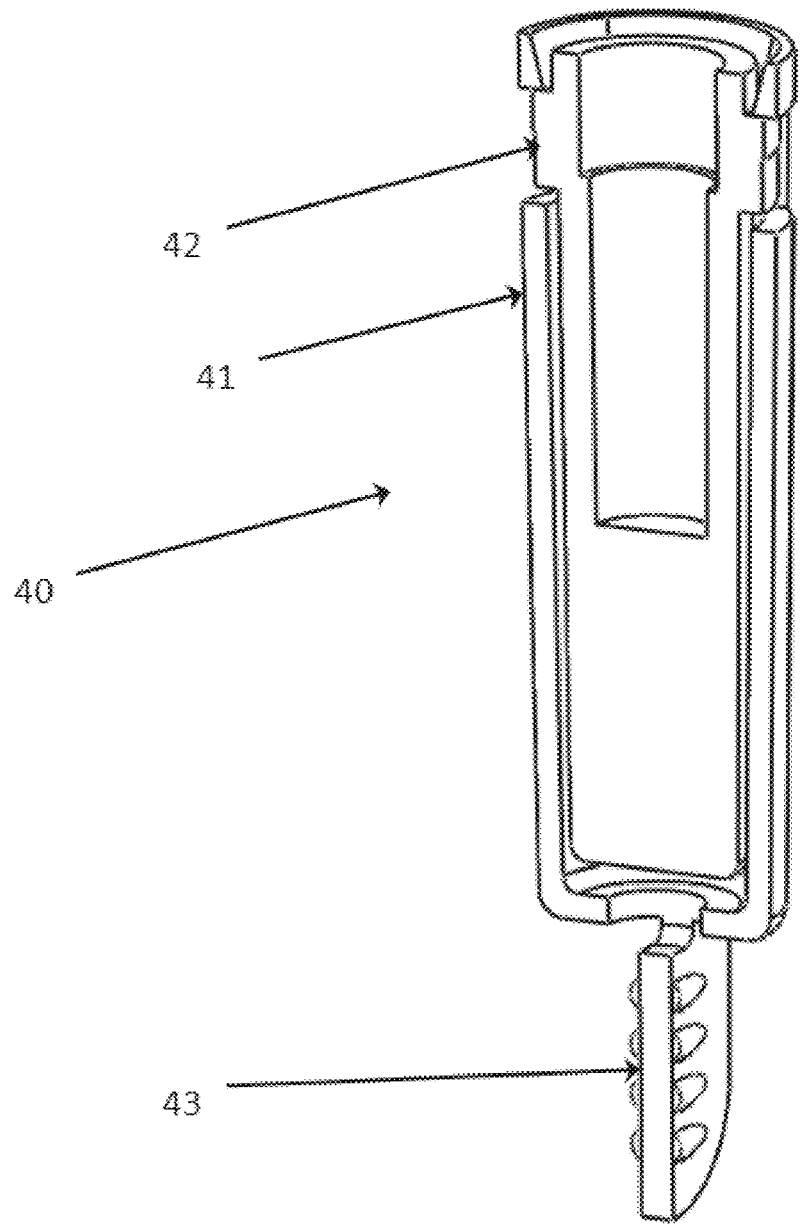
FIG. 11 is an isometric cross sectional view of the RNS.

Turning to FIGS. 7, 8 and 9, the device 100 is shown assembled to the syringe 50 via a recess 52 in the syringe neck 53 and lock collar tabs 11 located on the inner diameter of the lock collar 10. The rigid needle shield 40 is attached to the distal end of the syringe 54. As shown in FIGS. 10 and 11, the rigid needle shield 40 is comprised of an outer rigid thermoplastic 41, and inner soft elastomeric needle shield 42, as is currently marketed and often used on glass, pre-filled syringes to protect the needle and drug such as, e.g., the Stelmi rigid needle shield or the BD rigid needle shield. The distal end of the syringe 54 is designed to be identical to a standard 1 ml long pre-filled glass syringe. Consequently, the rigid needle shield 40 functions identically to current pre-filled syringe rigid needle shield systems, protecting both the needle sharp 51 and the contents of the syringe 50 by creating a seal between the soft needle shield component 42 and the bulbus 55 of the syringe, and the soft needle shield component 42 and the syringe sharp 51.

The rigid needle shield 40 also contains a grip section 43 extending from the outer rigid portion 41, which protrudes from the bottom of the device shield 20 as depicted in FIG. 7. The grip 43 is available to the user to grab and remove the rigid needle shield 40 prior to use of the syringe 50 and safety device 100. After removal of the rigid needle shield 40, the syringe 50 and safety device 100 is ready for drug injection.

Figure 12:
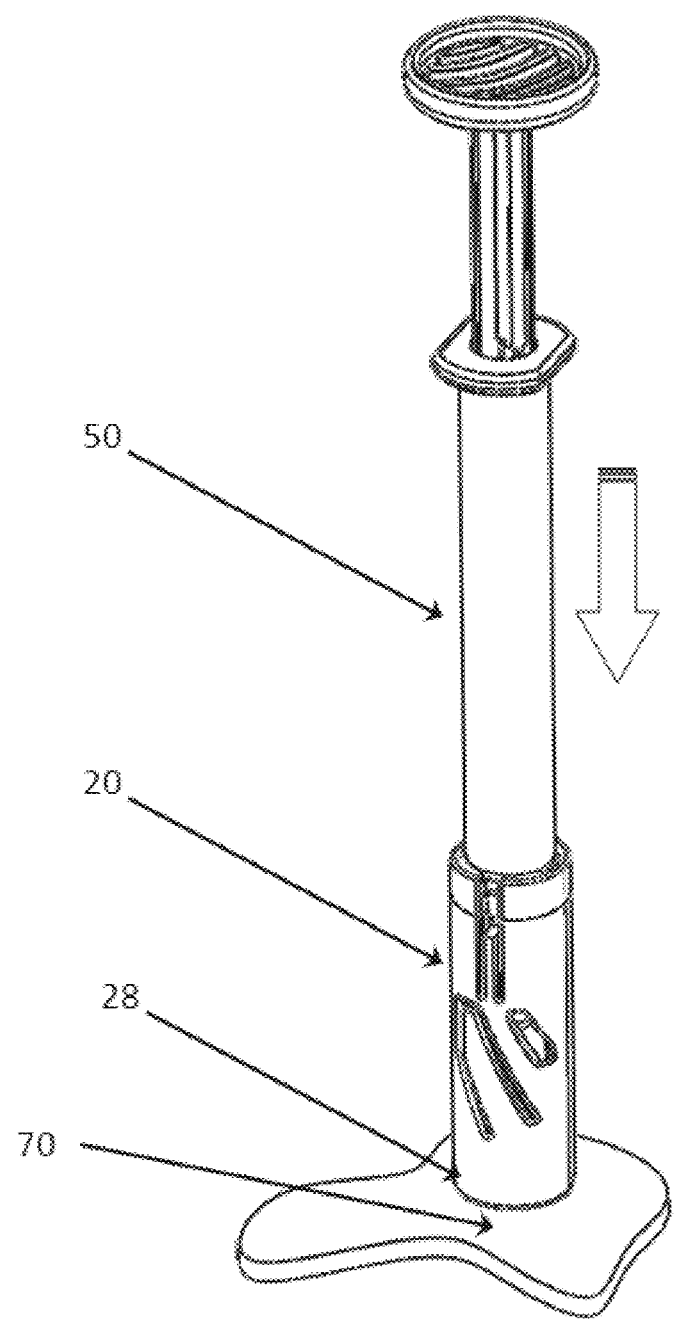
FIG. 12 is an isometric view of the safety device fully assembled with a syringe and a plunger, and with the RNS removed. The device is depicted as pressed against the skin of a patient ready to insert the needle into the injection site.
Figure 13:
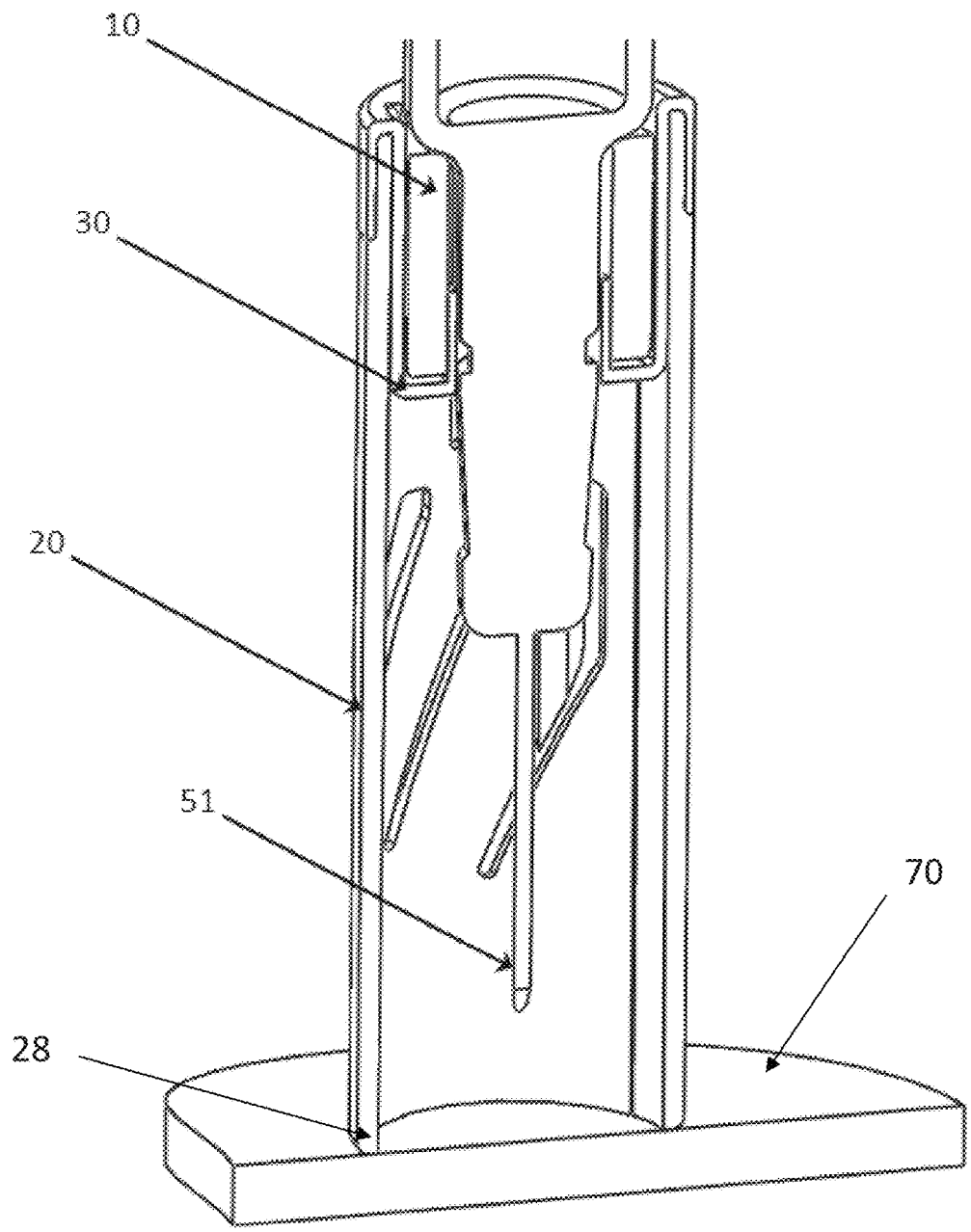
FIG. 13 is a cross sectional, partial isometric view of the safety device fully assembled with a syringe, and with the RNS removed. The safety device is depicted as pressed against the skin of a patient ready to insert the needle into the injection site.

Turning to FIG. 12, to perform an injection a user would place the distal end 28 of the device shield 20 against the injection site 70 and push the syringe 50 to insert the needle 51. As the syringe 50 is pushed distally, the device shield 20 will travel proximally along the syringe 50. As shown in FIG. 13, the flexible interconnect 30 is bonded or fixed to the distal end of the lock collar 10 and to the proximal end of device shield 20, and, as a result, as the syringe 50 is pushed distally, the lock collar 10, which is coupled to the syringe 50, travels distally relative to the device shield 20 causing the flexible interconnect 30 to be stretched, thereby storing energy, and thus, acting like a spring.

Figure 14:
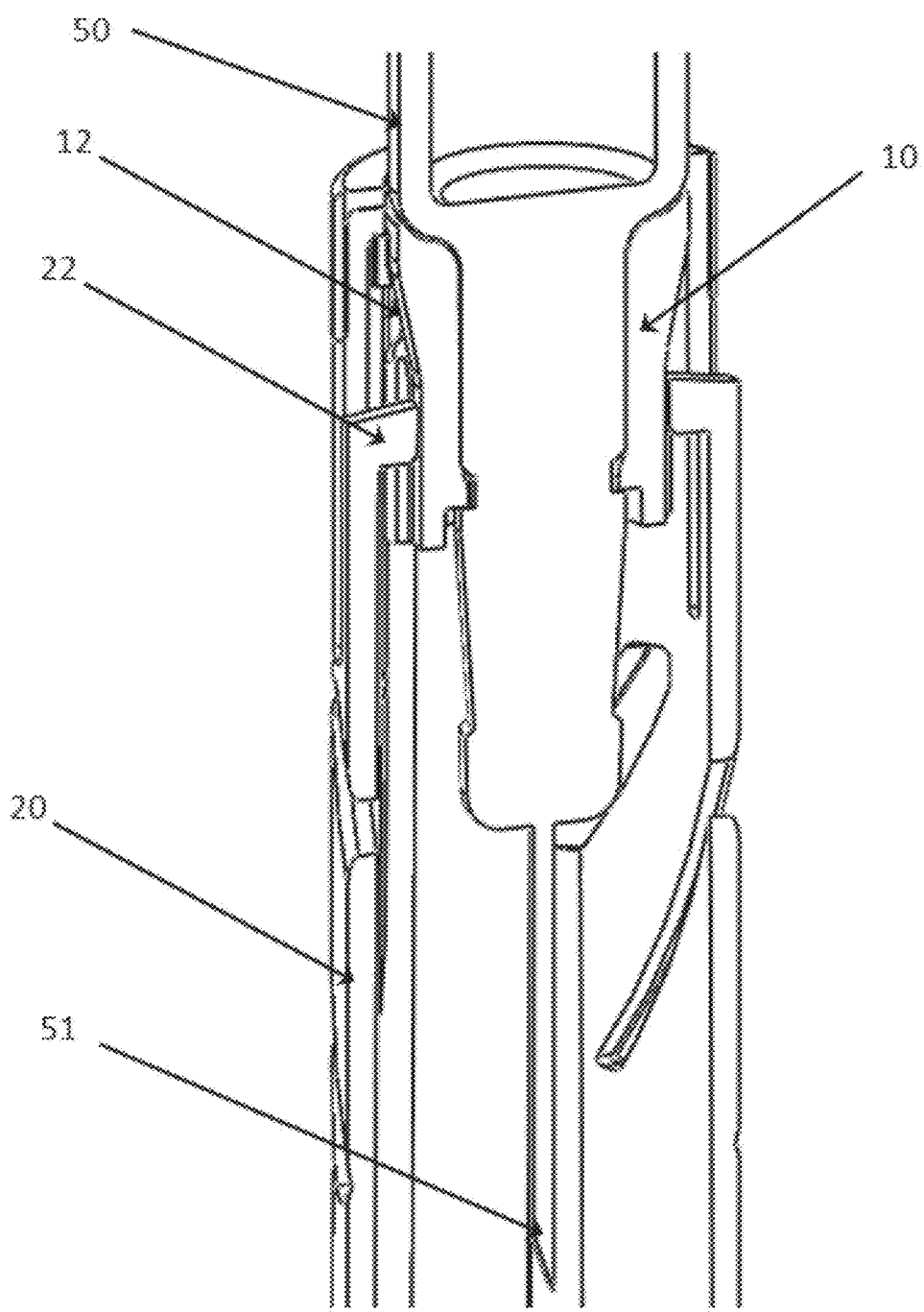
FIG. 14 is a cross sectional, isometric view of the device prior to inserting the needle into the injection site showing a ramp within the lock collar which device shield lock arms travel up.
Figure 15:
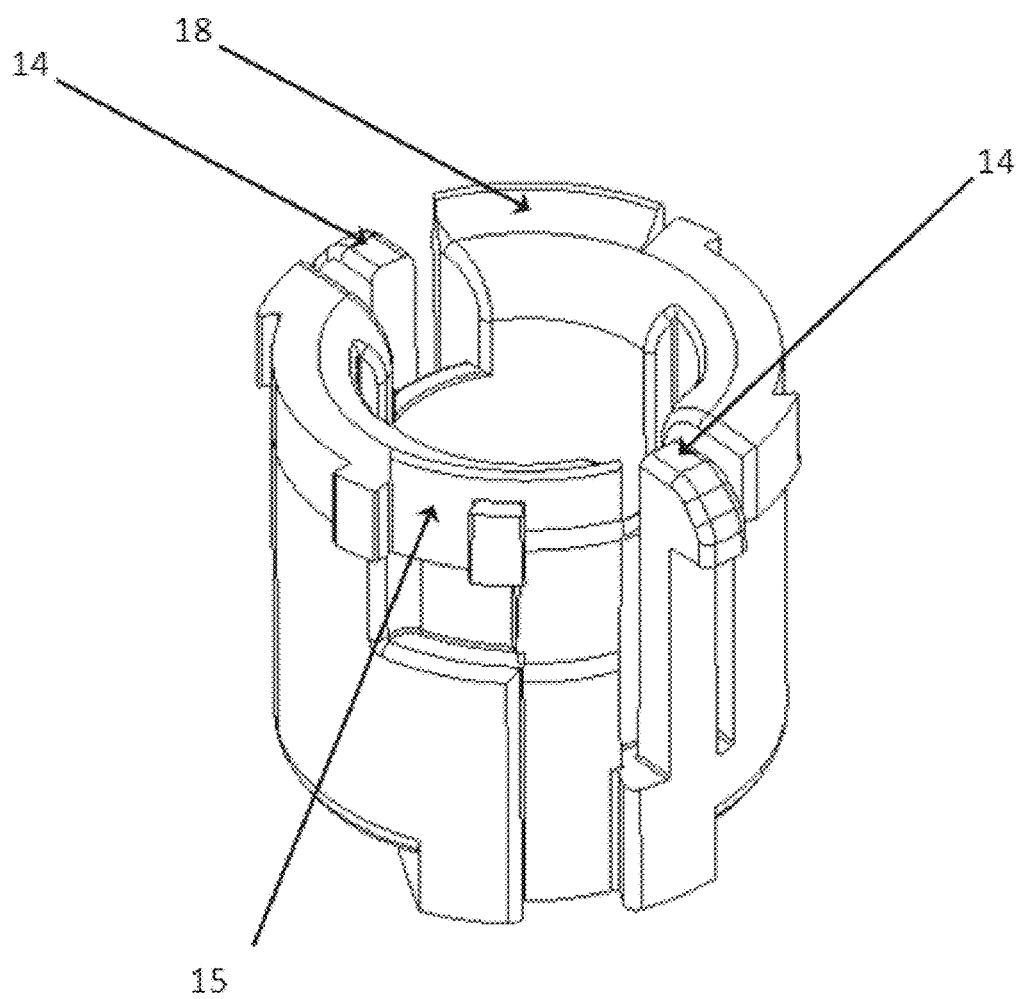
FIG. 15 is an isometric view of the lock collar.
Figure 16:
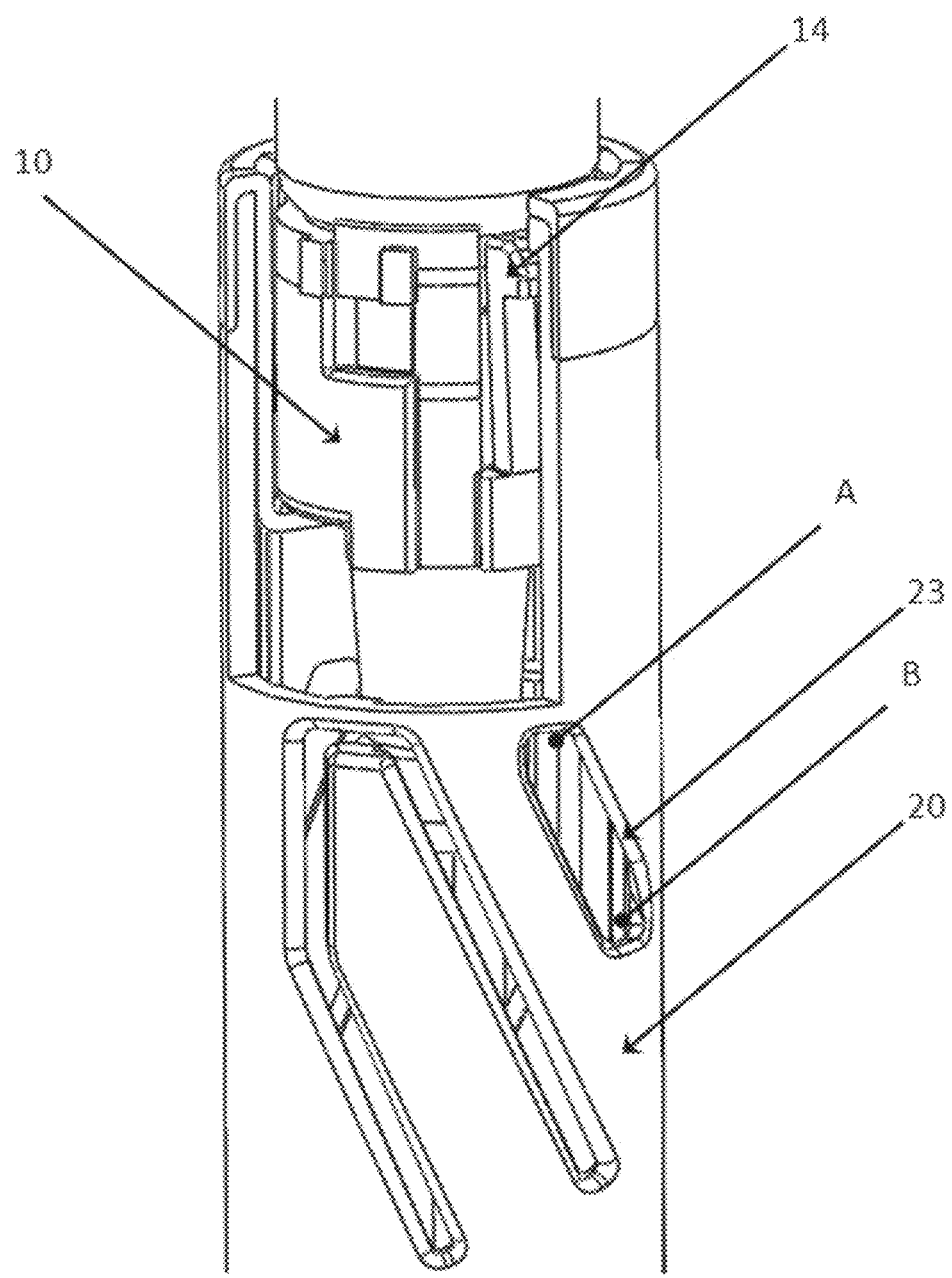
FIG. 16 is an isometric view of the safety device prior to needle insertion into the injection site with a portion of the device shield and flexible interconnect cut away. This view shows a lock collar rotation arm and its alignment with an angled cutout within the device shield.
Figure 17:
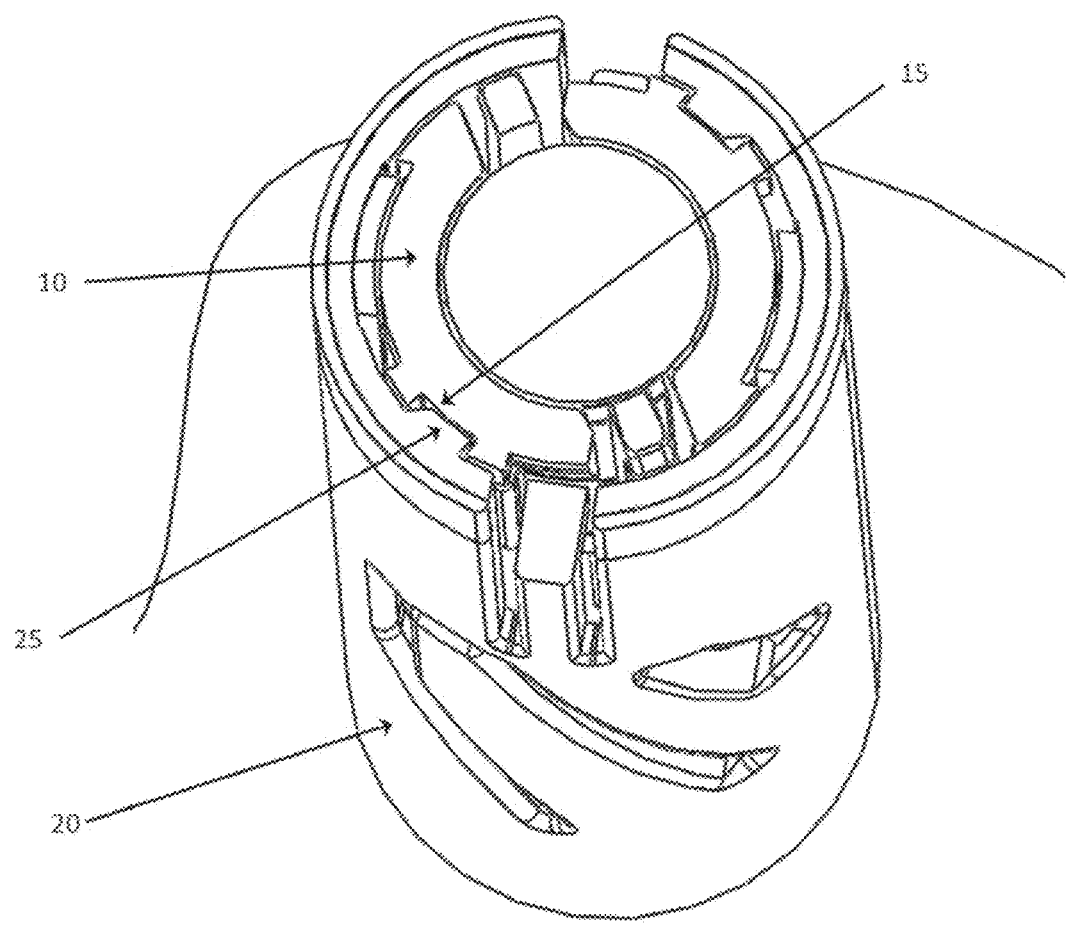
FIG. 17 is a cross sectional view through the top of the safety device revealing the rotational dependence of the device shield and lock collar via a key on the device shield and a keyway within the lock collar.
Figure 18:
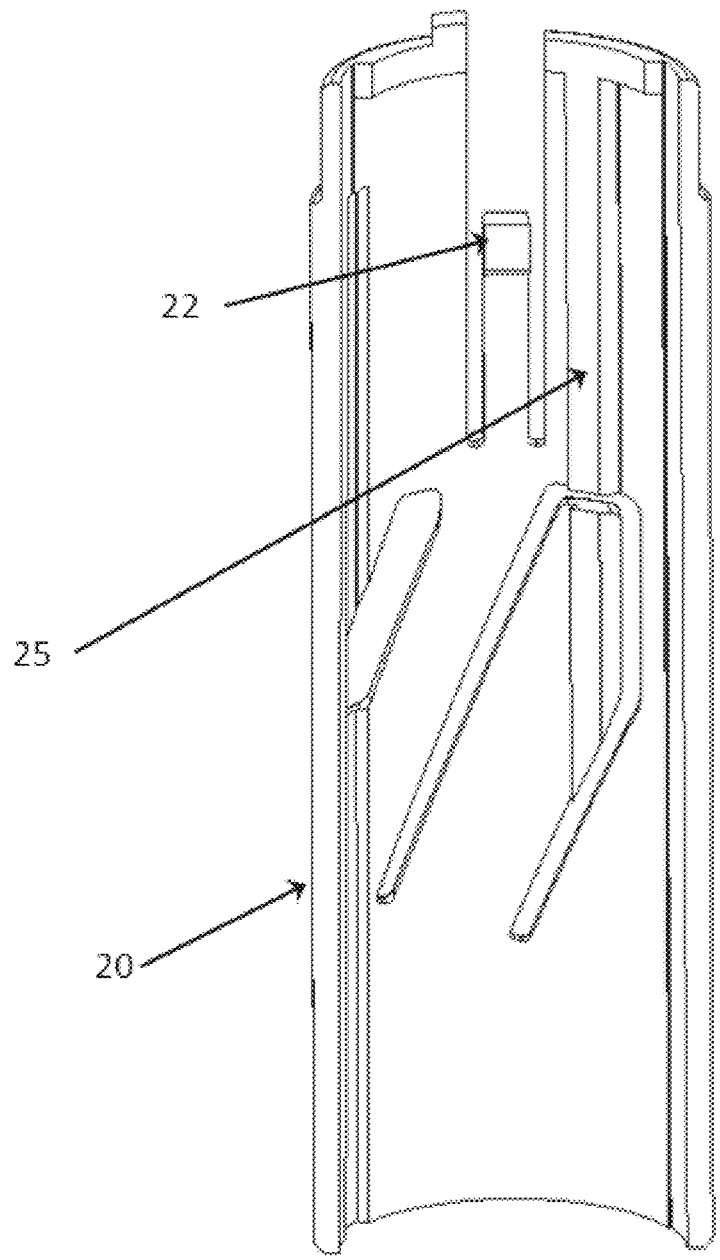
FIG. 18 is a cross sectional isometric view of the device shield.
Figure 19:
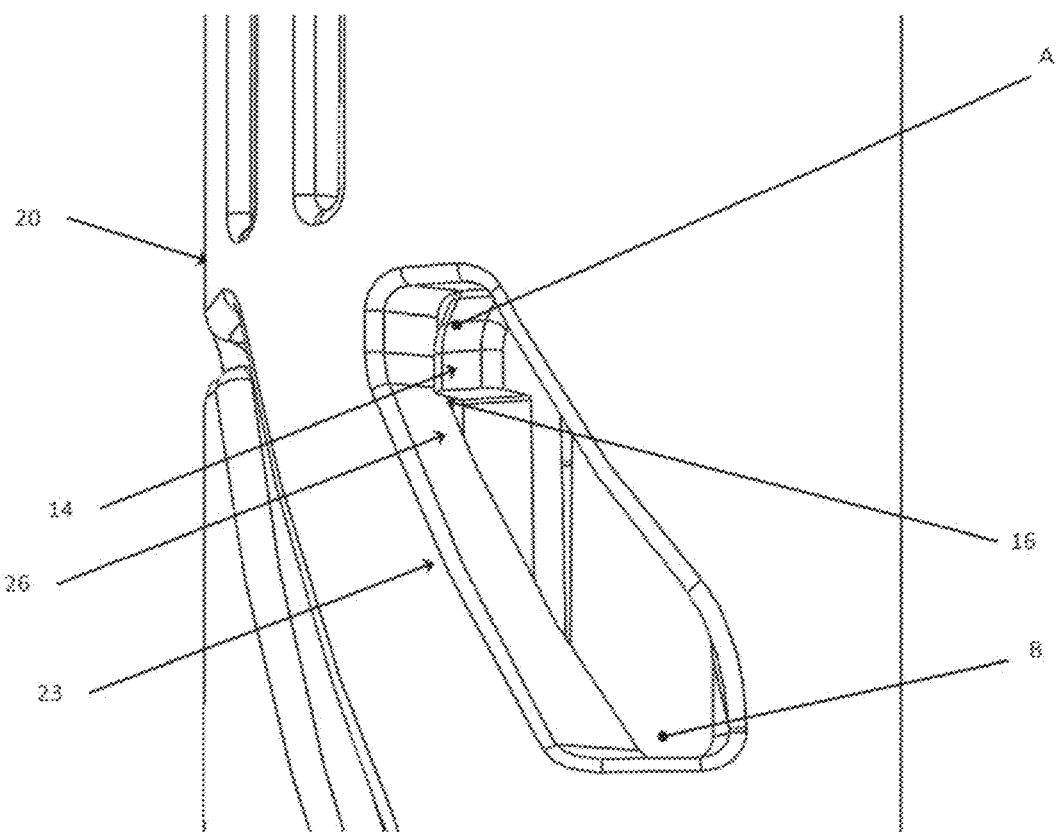
FIG. 19 is an isometric detail view of the lock collar rotation arm as it has engaged with the device shield angled cutout during needle insertion.
Figure 20:
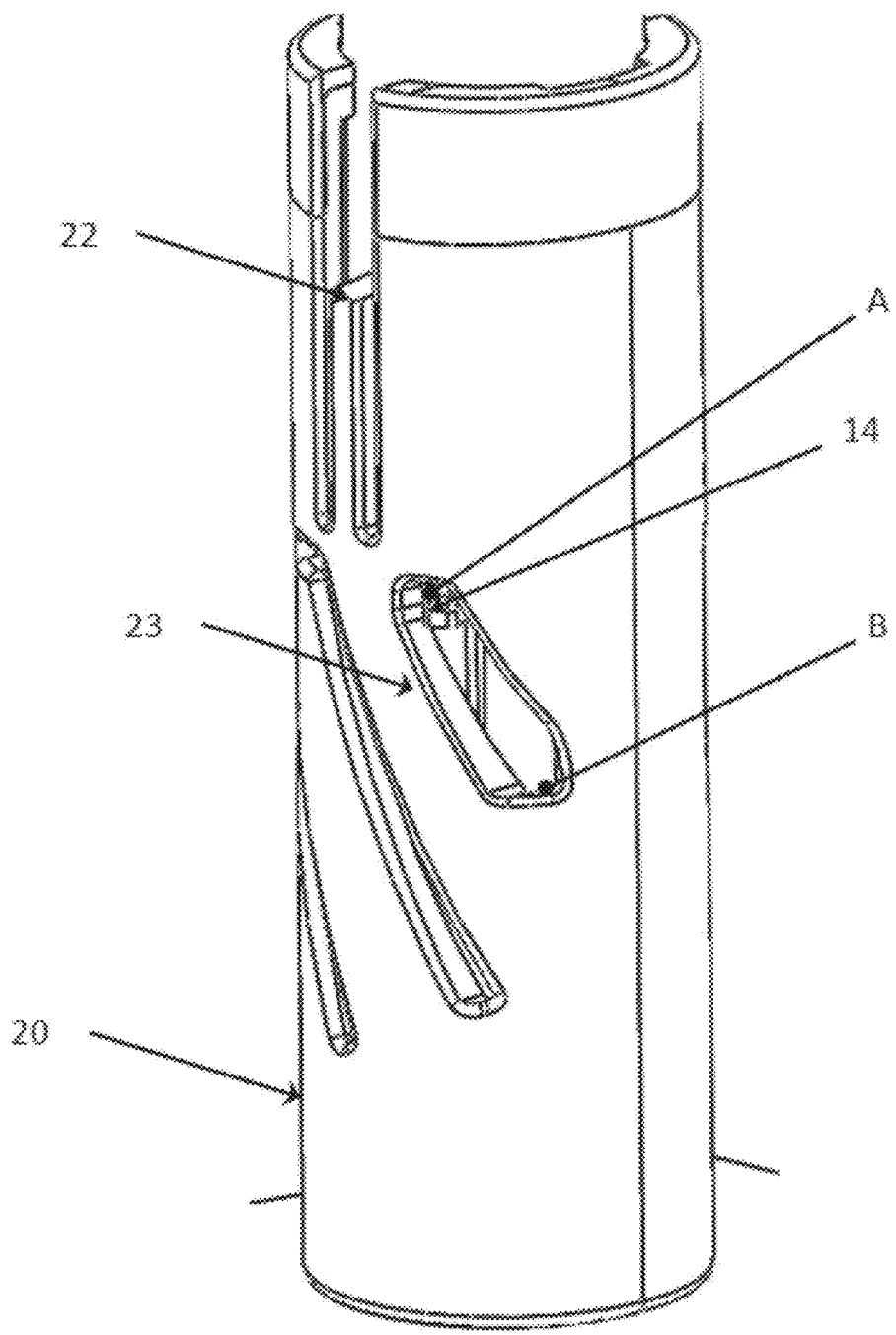
FIG. 20 is an isometric view of the safety device during needle insertion as the lock collar rotation arm has engaged with the device shield angled cutout during needle insertion.
Figure 21:
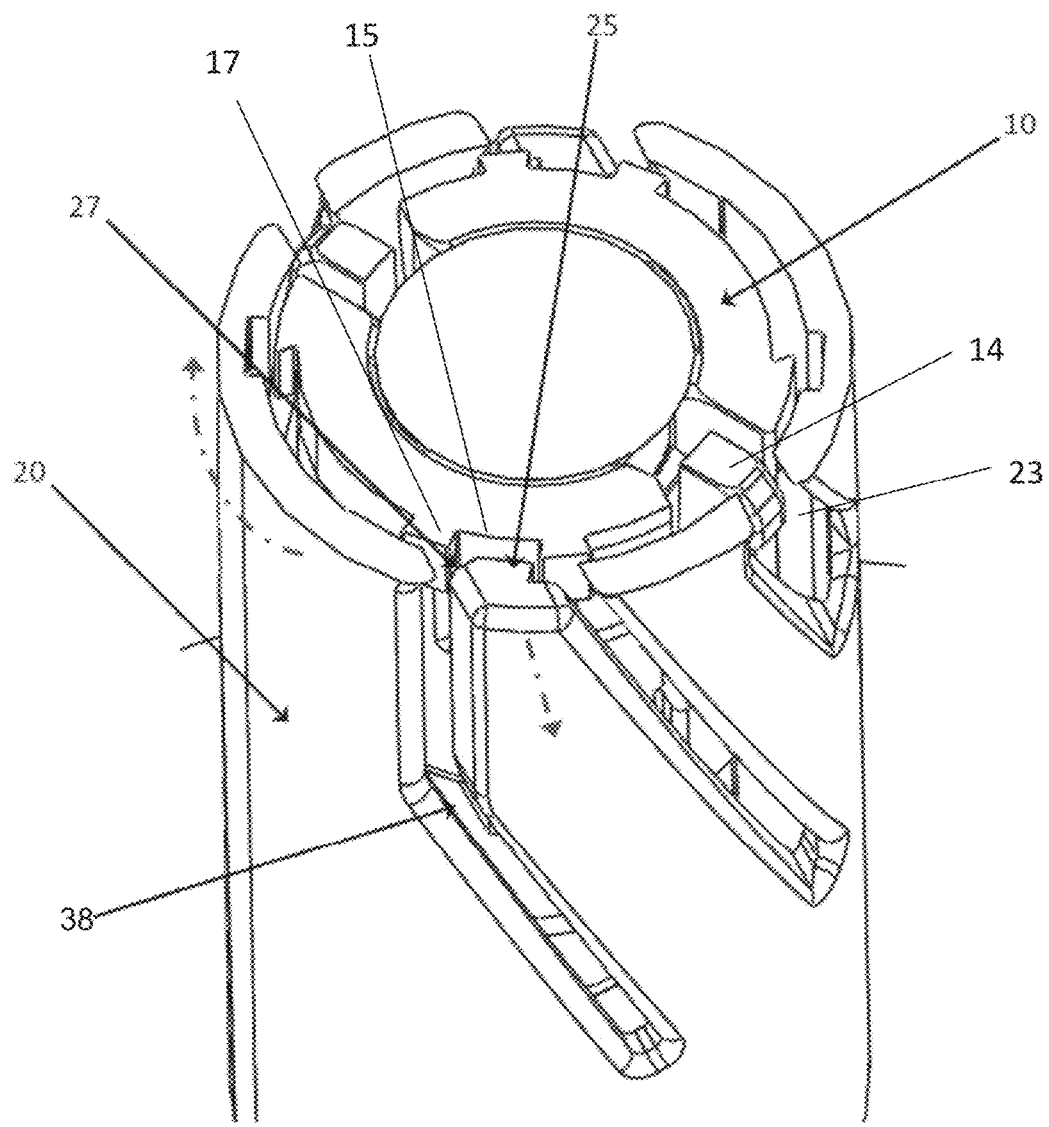
FIG. 21 is an isometric, cross sectional view through the safety device during needle insertion which shows the direction of rotation of the device shield relative to the lock collar and the device shield key's ability to flex from the keyway at the point of needle insertion.
Figure 22:
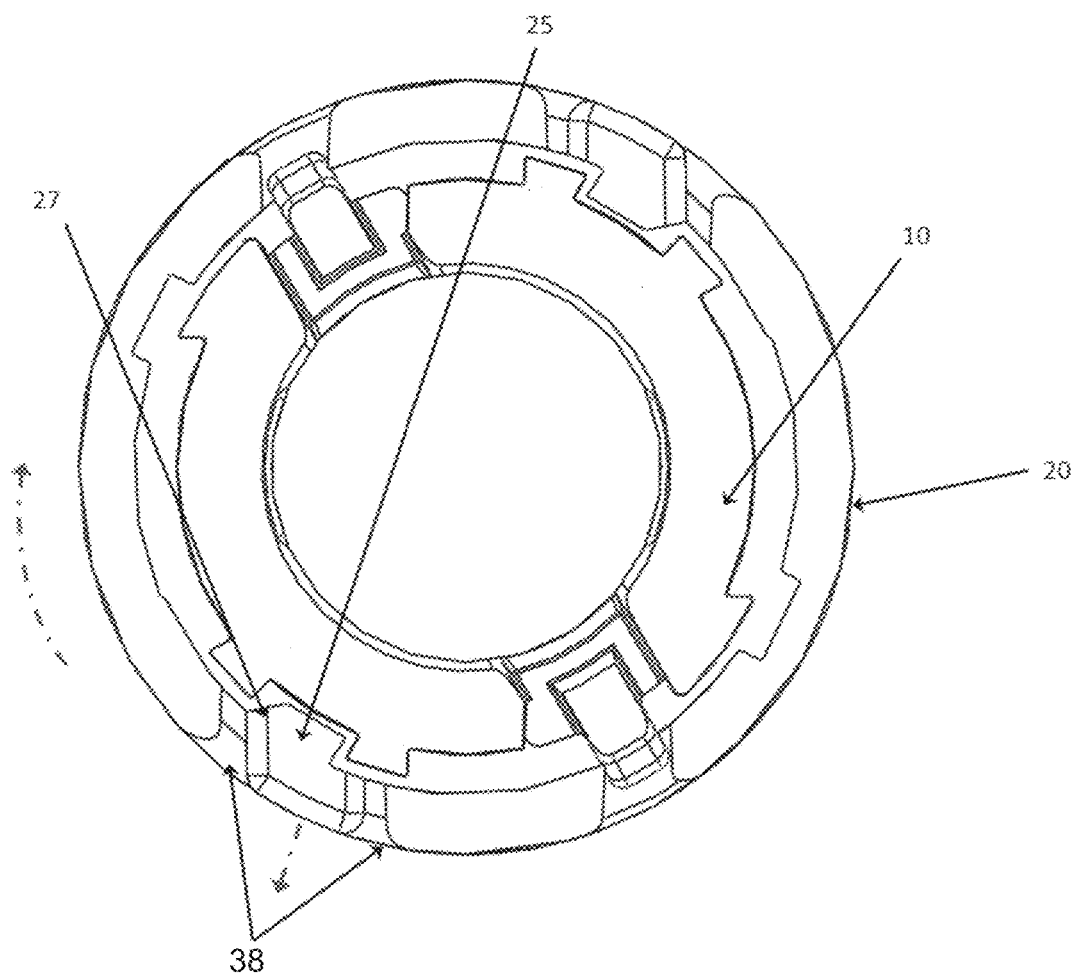
FIG. 22 is a, cross sectional view viewed from the proximal end through the safety device during needle insertion which shows the direction of rotation of the device shield relative to the lock collar and the device shield key's ability to flex from the keyway at the point of needle insertion.

During the initial few millimeters of travel of the device shield 20 proximally along the syringe 50, a device shield lockout arm 22 rides up or proximally along a ramp 12 located on the lock collar 10 as shown in FIG. 14. Consequently, the device shield lockout arm 22 flexes and will ride up or proximally along the syringe 50 in flexion during insertion of the needle 51 into the injection site 70. Turning to FIGS. 15 and 16, an angled cutout 23 is shown in the device shield 20 and a rotation arm 14 is shown on the lock collar 10. The rotation arm 14 is aligned vertically with the beginning point (Point A) of the angled cutout 23. As depicted in FIGS. 17 and 18, prior to needle 51 insertion, the lock collar 10 and device shield 20 are rotationally coupled via keys 25 axially extending along the interior of the device shield 20 and keyways 15 located on the outer periphery of the lock collar 10. Turning to FIGS. 19 and 20, when the device shield 20 has travelled up or proximally along the syringe 50 a sufficient predetermined distance, such that the rotation arm 14 of the lock collar 10 reaches point A of the angled cutout 23, the rotation arm 14, which is in a flexed state while inside of the device shield 20, will resile into the angled cutout 23 in the device shield 20. As a result of the contact now made between the angled cutout surface 26 and the bottom edge 16 of the rotation arm 14, and the continued proximal movement of the device shield 20 relative to the syringe 50, the device shield 20 and lock collar 10 will begin to rotate relative to one another. As depicted in FIGS. 21 and 22, as the device shield 20 and lock collar 10 rotate relative to one another as the needle 51 is further inserted into the injection site 70, an angled or chamfered surface 27 on the device shield key 25 and a cutout 38 within the device shield 20 allows the device shield key 25 to flex out from the keyway 15 and travel over a lock collar tab 17.

Figure 23:
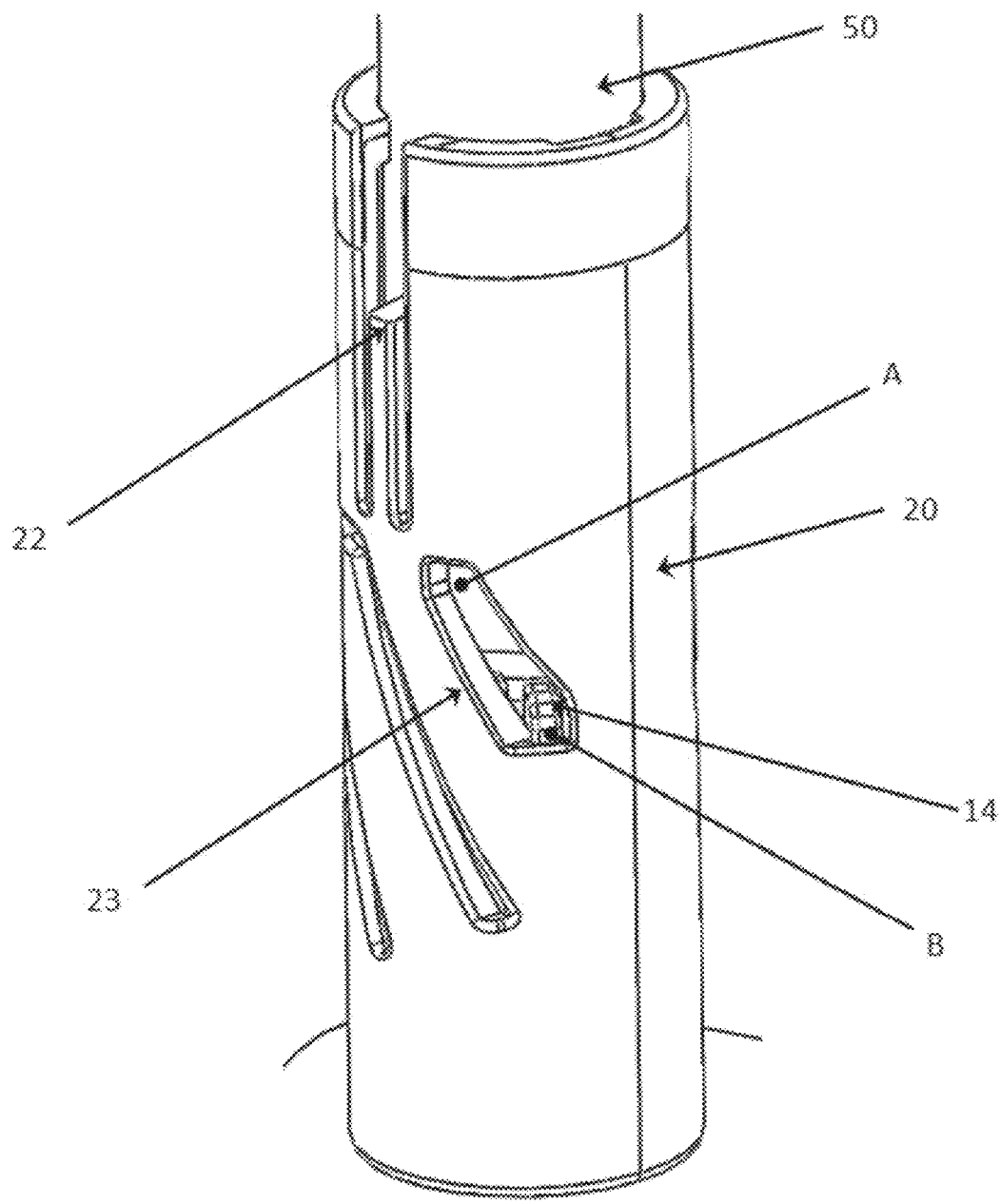
FIG. 23 is an isometric view of the safety device at full needle insertion with the lock collar rotation arm at point B of the device shield angled cutout.
Figure 24:
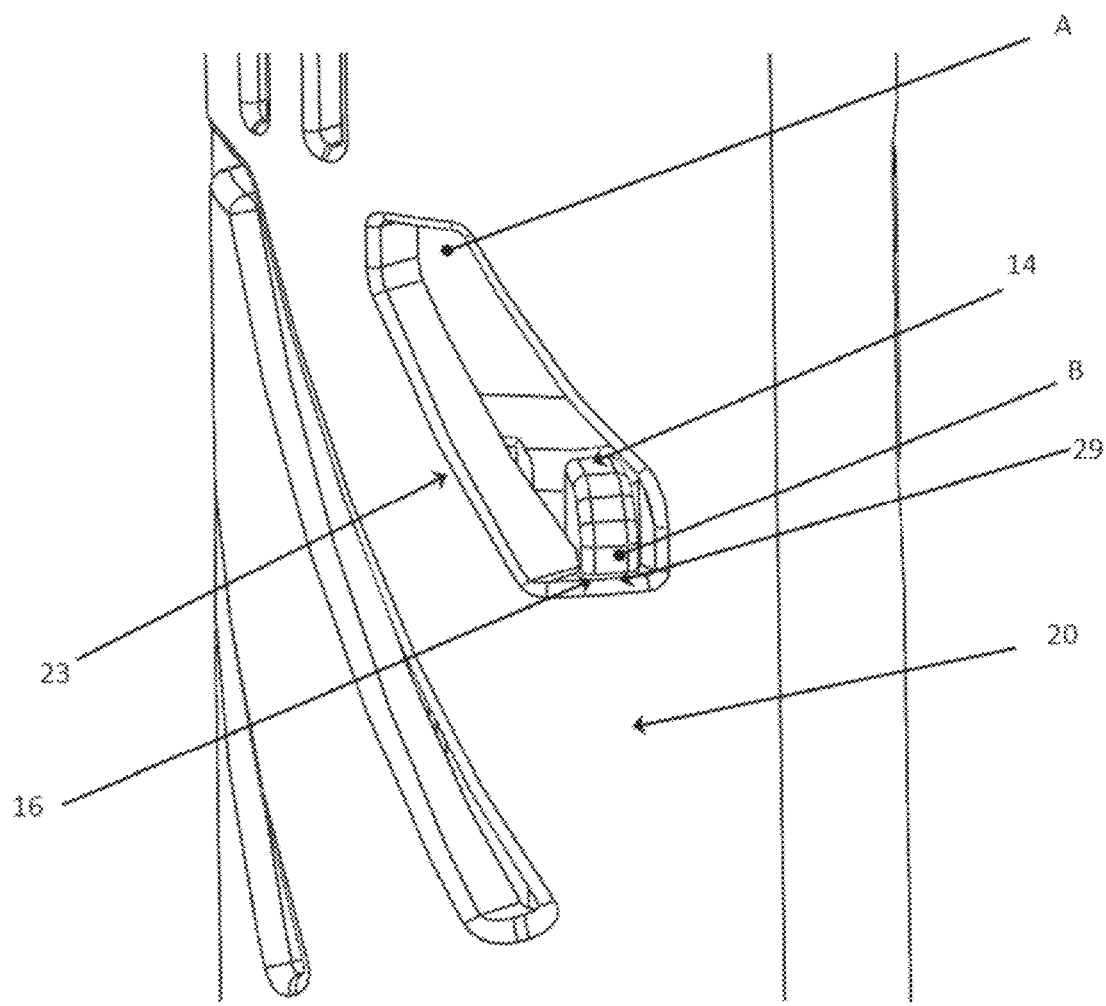
FIG. 24 is a detail view of the lock collar rotation arm at point B of the device shield angled cutout at full needle insertion.
Figure 25:
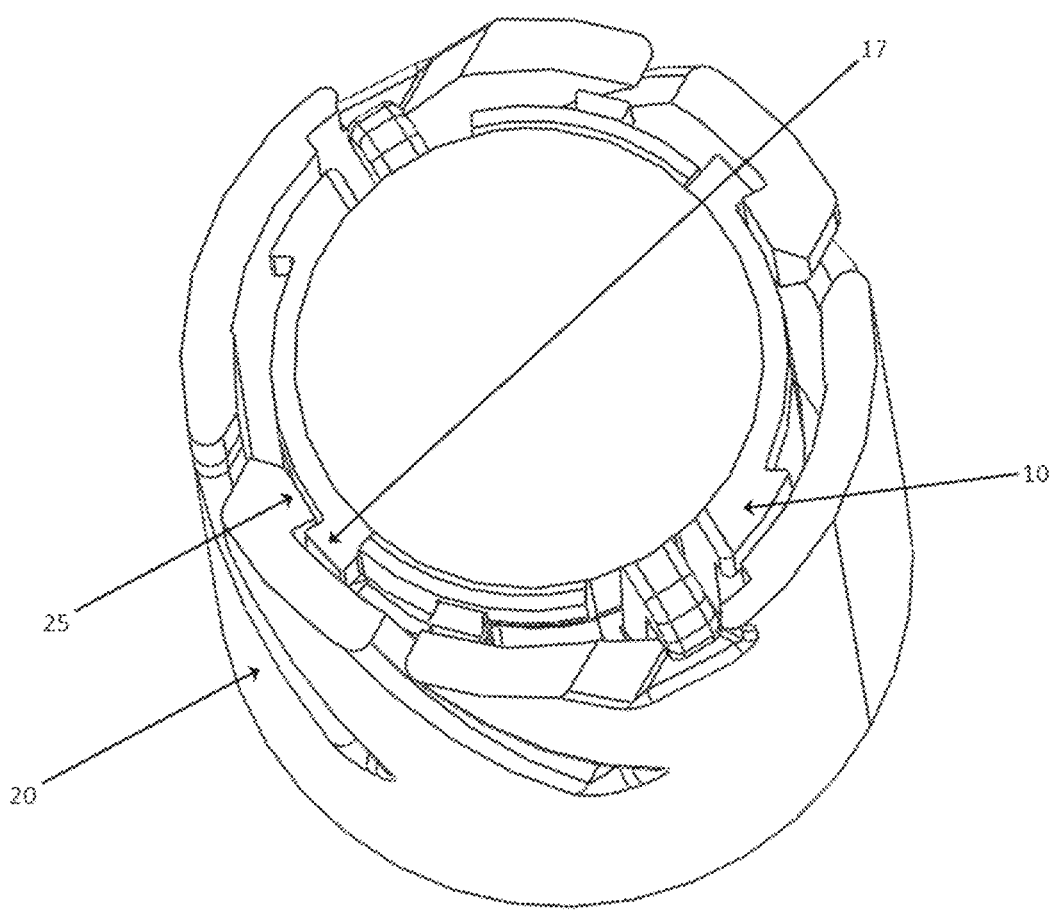
FIG. 25 is an isometric, cross sectional view of the safety device after full needle insertion, showing the device shield key locked rotationally with the lock collar tab.

Referring to FIGS. 23 and 24, at the point where the lock collar rotation arm 14 reaches point B in the angled cutout 23, the needle 51 is fully inserted into the injection site 70, the device shield 20 cannot move up or proximally along the syringe 50 any further due to the interface between the bottom surface 16 of the rotation arm 14 and the bottom surface 29 of the angled cutout 23, and, as shown in FIG. 25, the device shield 20 and lock collar 10 are fixed rotationally as the key 25 is allowed to resile into engagement with a lock collar tab 17. It is preferable for the device shield 20 and lock collar 10 to be fixed rotationally at this point of device use, otherwise the torsion created in the flexible interconnect 30, as a result of twisting the device shield 20 in relation to the lock collar 10 during needle 51 insertion, would tend to force the device shield 20 and lock collar 10 to resile to their original orientations relative to one another upon needle 51 removal. Such an occurrence, would tend to prevent the device shield 20 from properly locking in a shielded position upon full needle removal 51 from the injection site 70.

Figure 26:
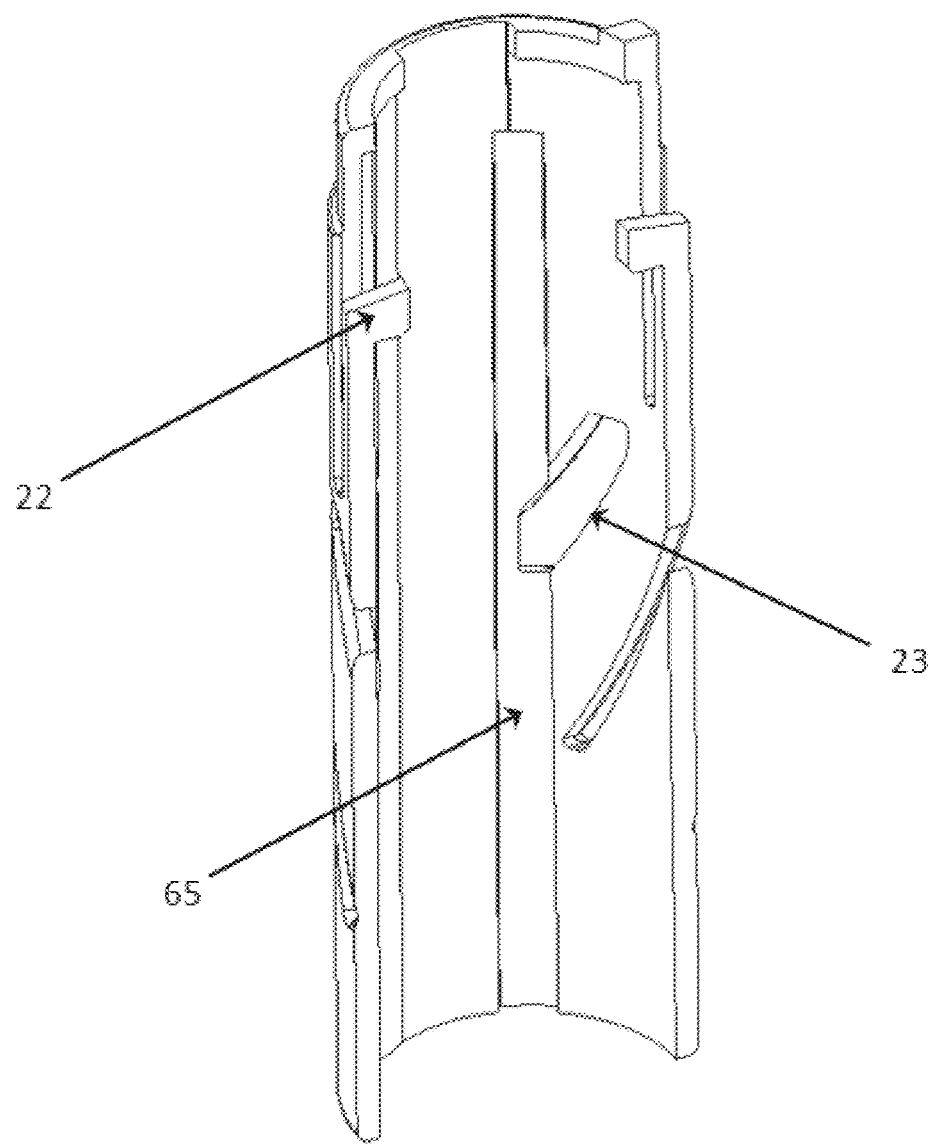
FIG. 26 is a cross sectional (90 degrees offset from FIG. 18) isometric view of the device shield.
Figure 27:
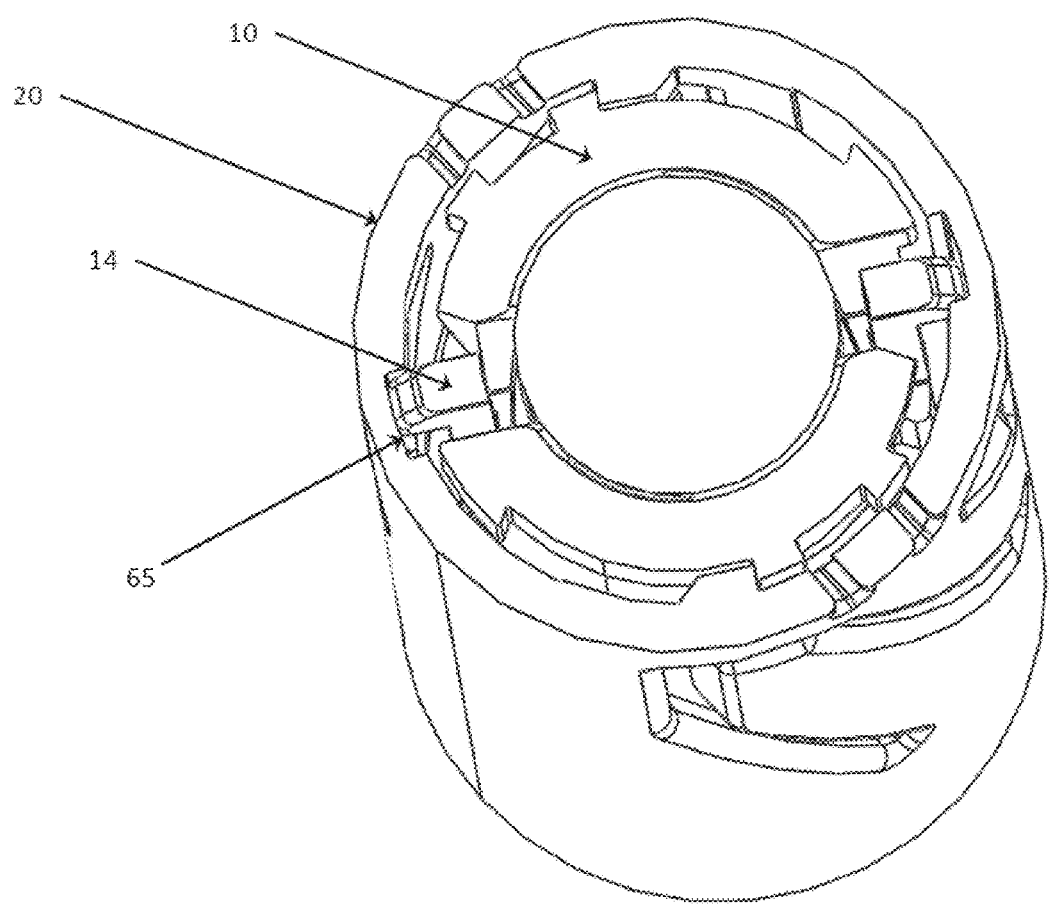
FIG. 27 is an isometric, cross sectional view of the safety device after full needle insertion, showing the device shield cutout, in place to relieve any stress on the lock collar rotation arm.

After an injection has been given and the syringe 50 is pulled away from the injection site 70, the stress or stored energy in the flexible interconnect 30 forces the device shield 20 to move distally back down the syringe 50. As a result, the device shield 20 is always shielding the needle 51, and consequently, protecting the administrator from accidentally sticking themselves with the needle 51. Turning to FIGS. 26 and 27, as the device shield 20 is forced back towards the distal end of the syringe 50, the rotation arm 14 rides in a channel 65 in the interior of the device shield 20. The purpose of the channel 65 is to keep the rotation arm 14 from being required to flex and consequently, create a resistive friction force between the rotation arm 14 and the device shield 20 during needle 51 shielding.

Figure 28:
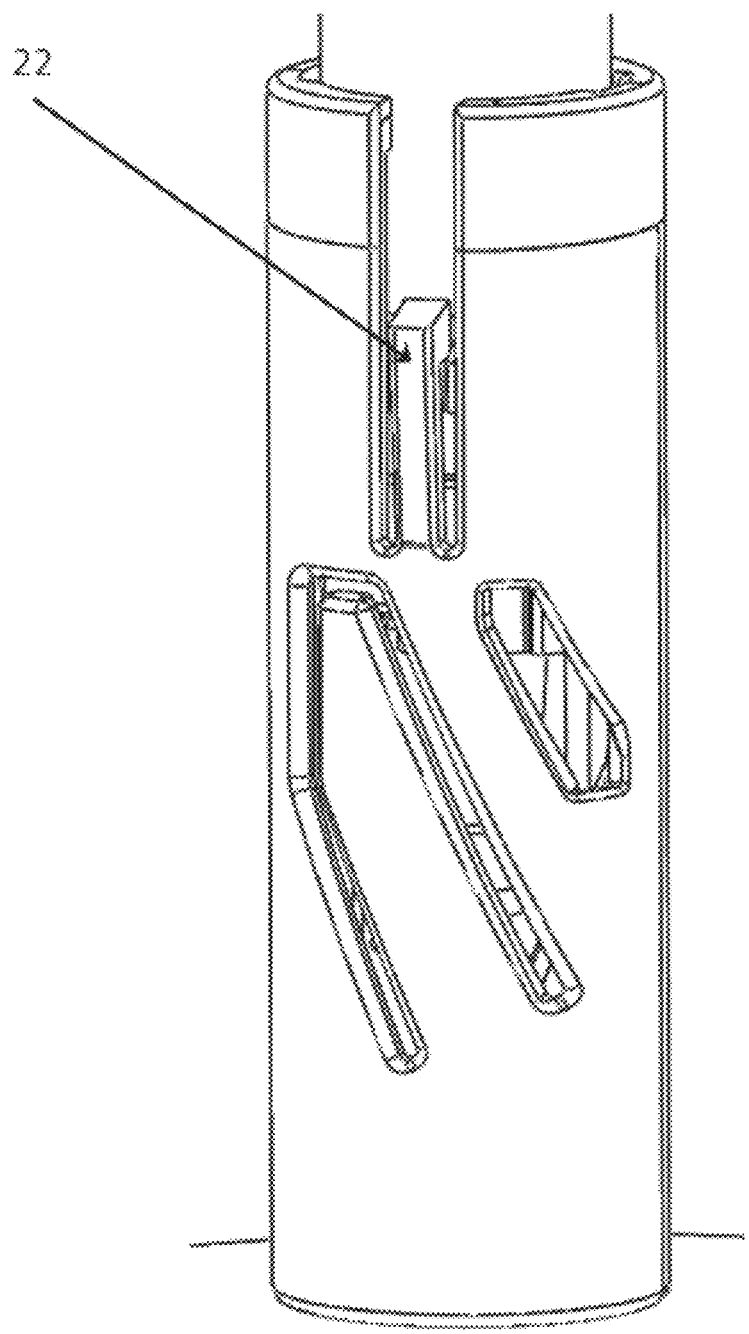
FIG. 28 is an isometric view of the safety device upon needle removal as a device shield lockout arm re-engages with the lock collar.
Figure 29:
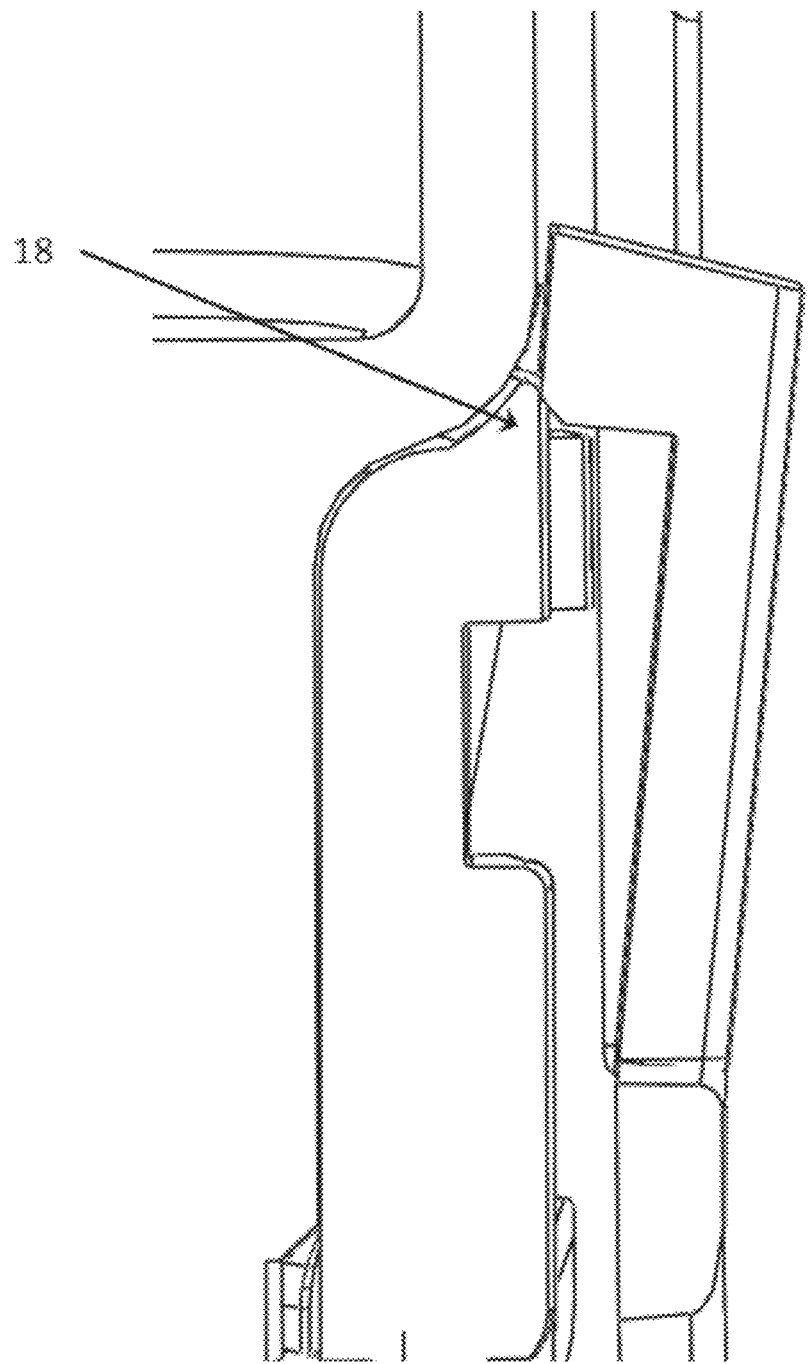
FIG. 29 is a detail, cross sectional view of the safety device upon needle removal as the device shield lockout arm re-engages with the lock collar.
Figure 30:
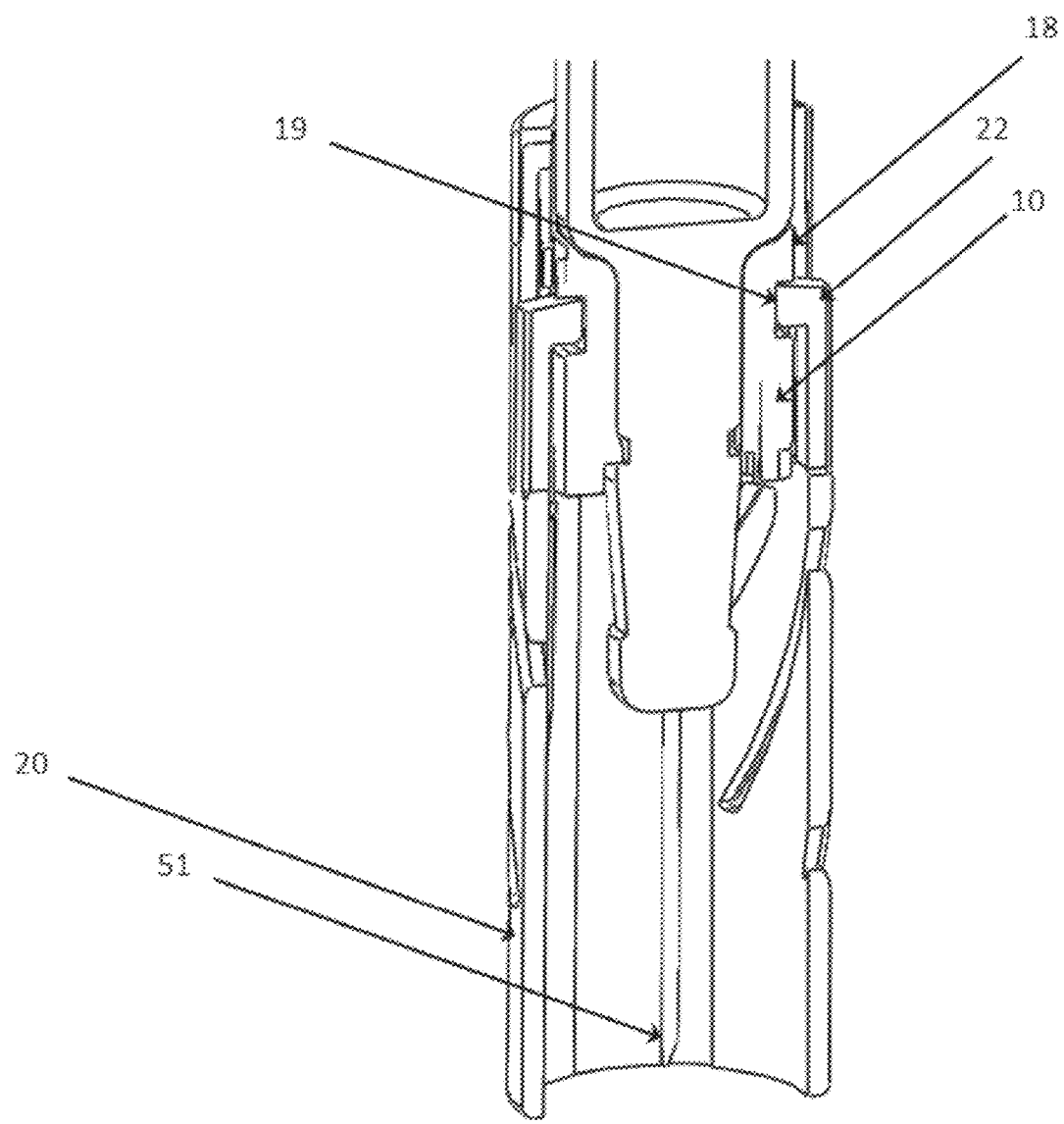
FIG. 30 is a cross sectional, partial isometric view of the device after needle removal and device lockout.
Figure 31:
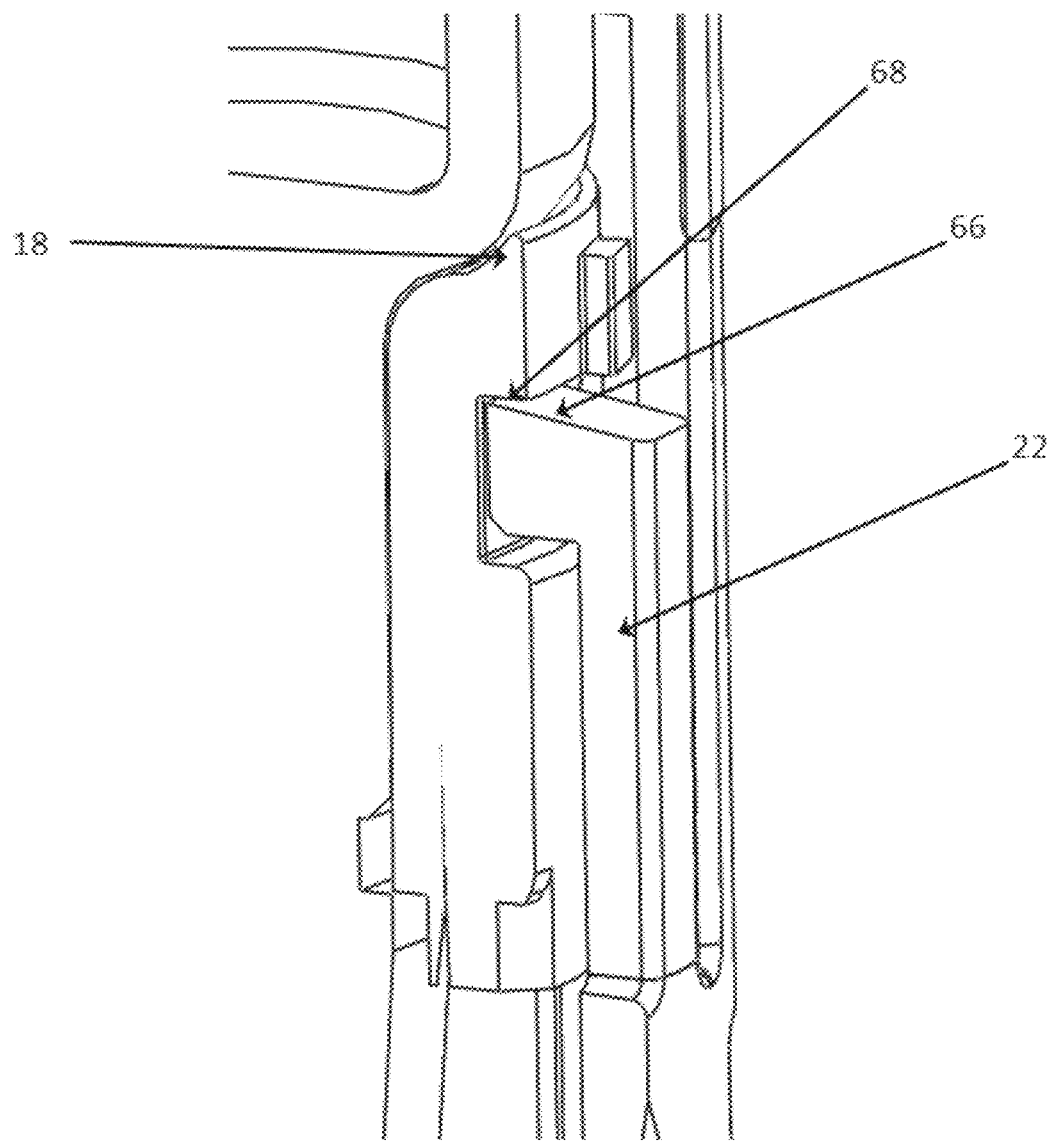
FIG. 31 is a detail, cross sectional, isometric view of the device after needle removal and device lockout with the device shield lockout arm in lockout position.

Furthermore, as shown in FIGS. 28 and 29, as the device shield 20 is forced back towards the distal end of the syringe 50 as a result of the force from the stretched flexible interconnect 30, the device shield lockout arm 22 rides in a flexed state along the surface of the syringe 50 and then along a lip 18 in the lock collar 10. As depicted in FIGS. 30 and 31, as the device shield lockout arm 22 rides distally down the lock collar lip 18 it will encounter a recess 19 in the lock collar, which it will snap into due to its flexed state. The interface between the top or proximal edge 66 of the device shield lockout arm 22 and the top or distal surface 68 of the lock collar recess 19 causes the device shield 22 to be in locked state, permanently protecting and shielding the needle 51. The interface between the bottom of lockout arm 22 and the bottom surface of the lock collar recess 19 prevents further distal movement of the device shield 20 relative to the syringe 50.

Figure 32:
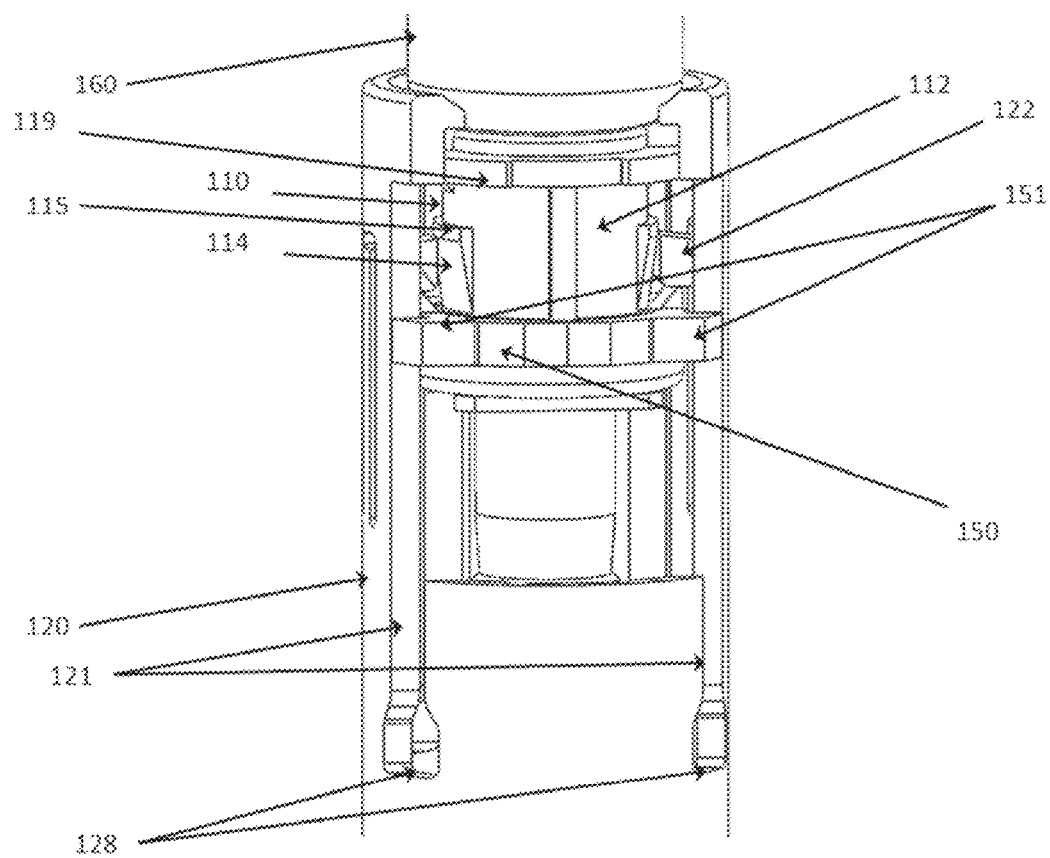
FIG. 32 is a partial isometric view of an alternate lockout method embodiment with a portion of the device shield cut away to view the inside of the device. The alternate lockout method embodiment is shown in a state prior to device use.
Figure 33:
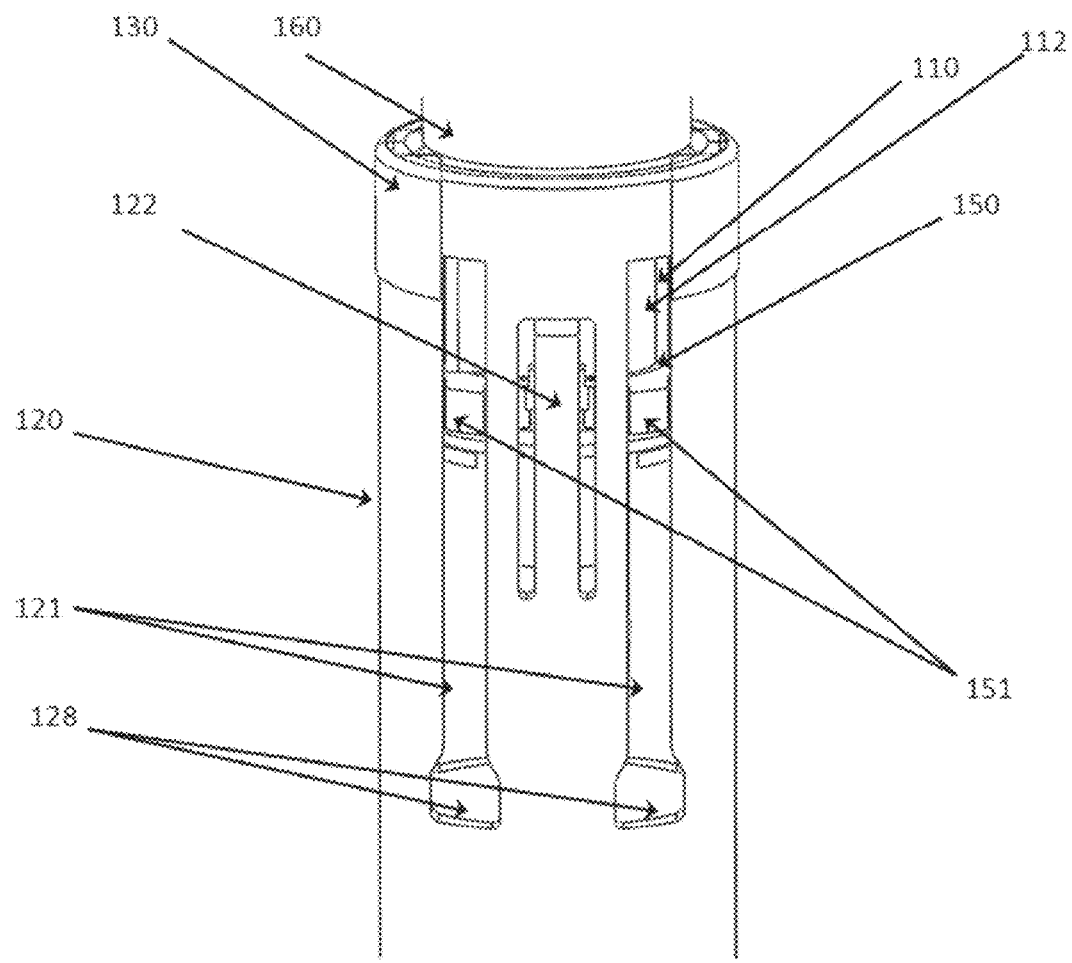
FIG. 33 is a partial isometric view of an alternate lockout method embodiment prior to device use.
Figure 34:
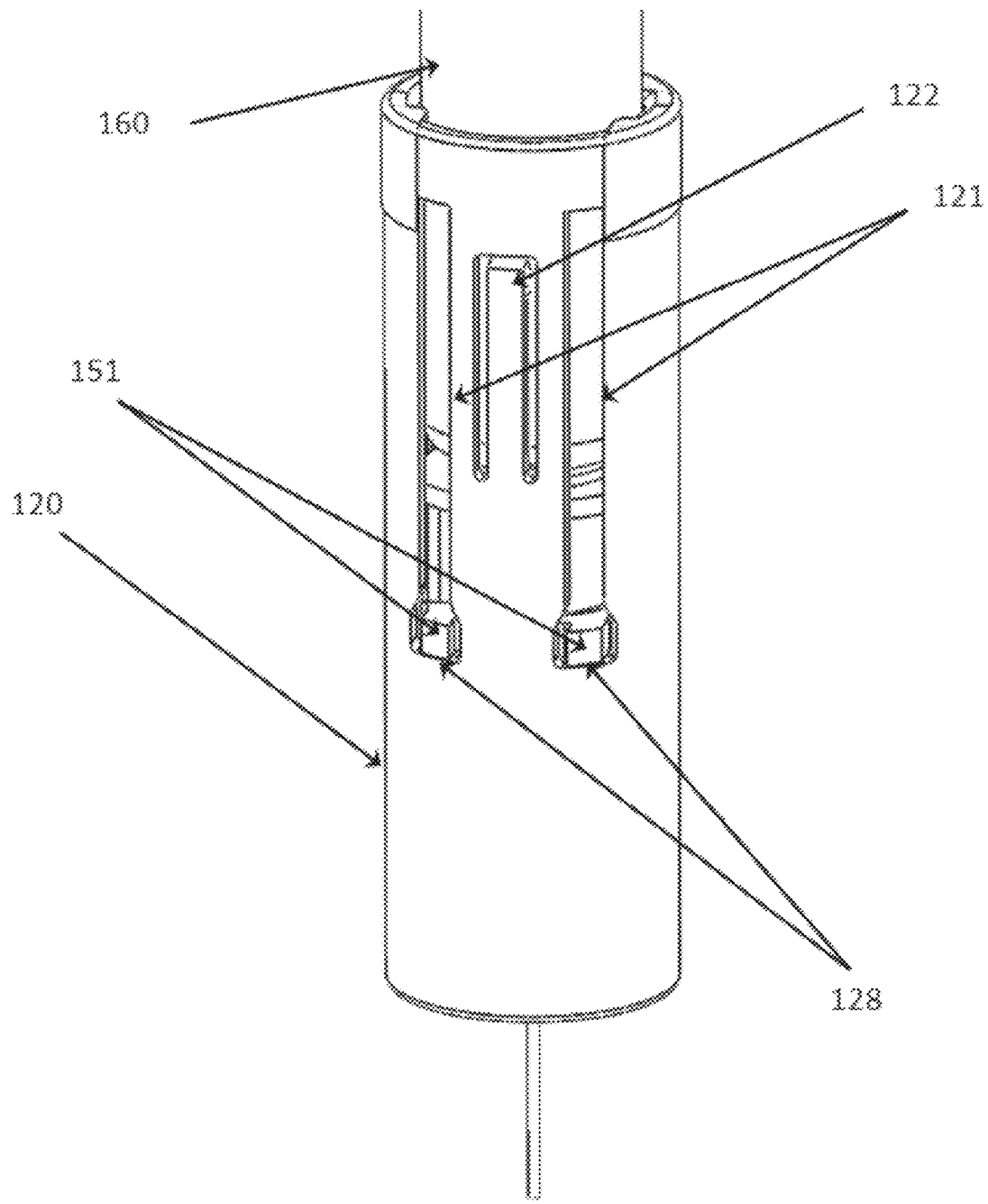
FIG. 34 is a partial isometric view of an alternate lockout method embodiment after the needle has been inserted partway into the injection site.
Figure 35:
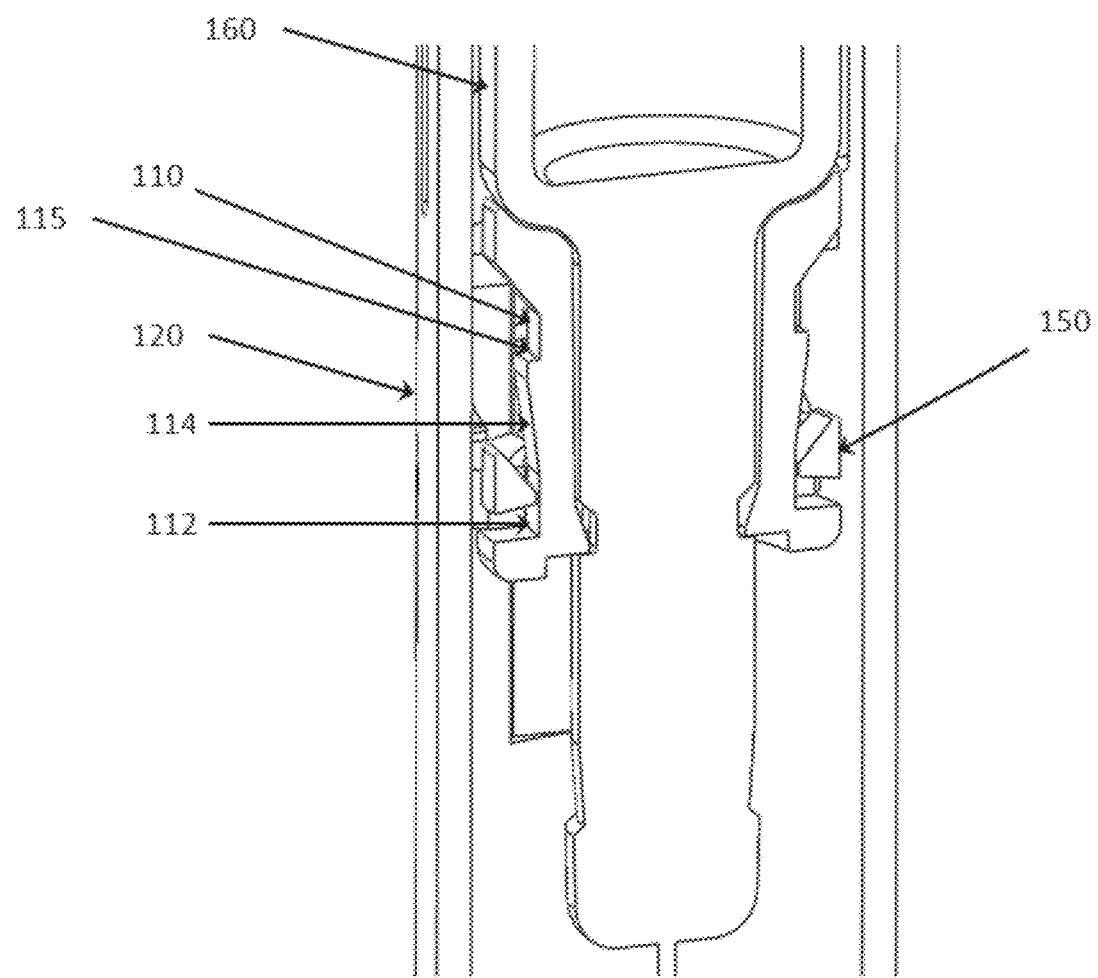
FIG. 35 is a cross sectional partial isometric view of the alternate lockout method embodiment after the needle has been inserted partway into the injection site.
Figure 36:
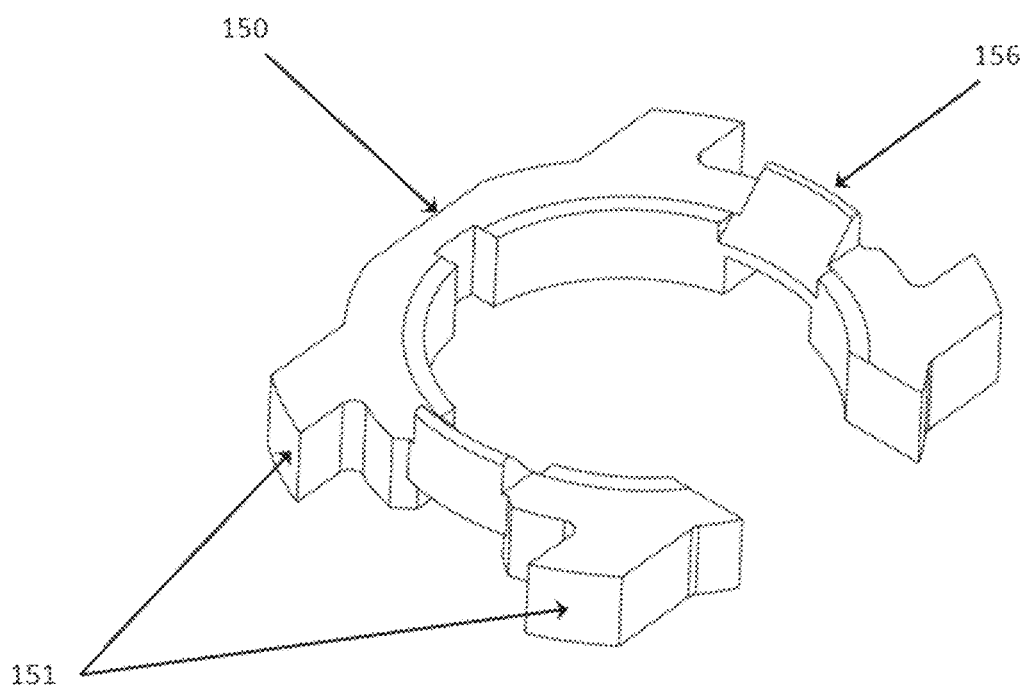
FIG. 36 is an isometric view of a lock ring used in the alternate lockout method embodiment.

Turning to FIGS. 32 and 33, an alternate embodiment is shown to include a different device lockout method. A lock ring 150 is assembled to the lock collar 110 at its distal end before device use. The lock ring 150 contains two tabs 151 on each side which sit within two channels 121 within the device shield 120. As shown in FIG. 34, during needle insertion the needle shield 120 moves proximally away from the injection site up the syringe 160 barrel such that the lock ring tabs 151 slide within the device shield channels 121 until the bottom surface 128 of the channels contact the lock ring tabs 151. As the device shield 120 continues to move up the syringe 160 barrel and the needle further penetrates the injection site, the lock ring 150, as depicted in FIG. 35, is carried with the device shield 120 up the shaft 112 of the lock collar 110 where it encounters a sloped ramp 114 on each side of the lock collar 110 and flexes over the sloped ramp 114. As shown in FIG. 36, the lock ring 150 is shaped like the letter C which makes it flexible.

Figure 37A:
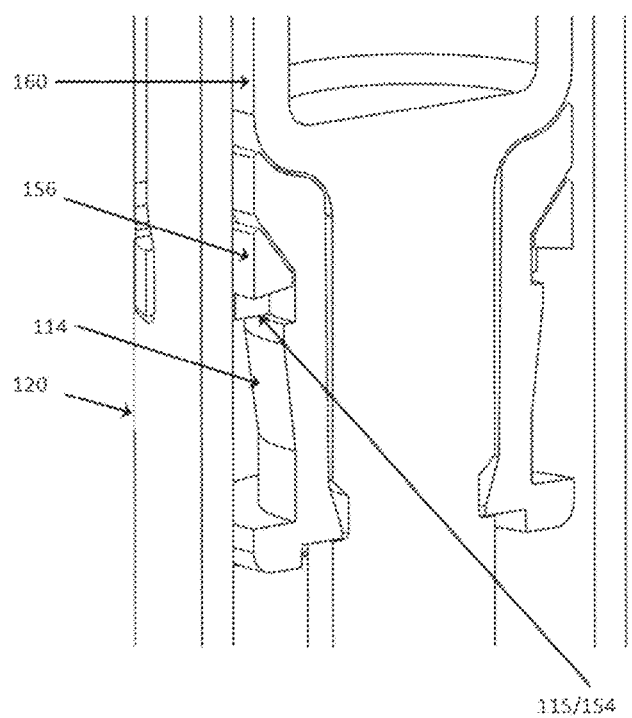
FIGS. 37A and B are cross sectional partial isometric views of an alternate lockout method embodiment after the needle has been inserted fully into the injection site.
Figure 37B:
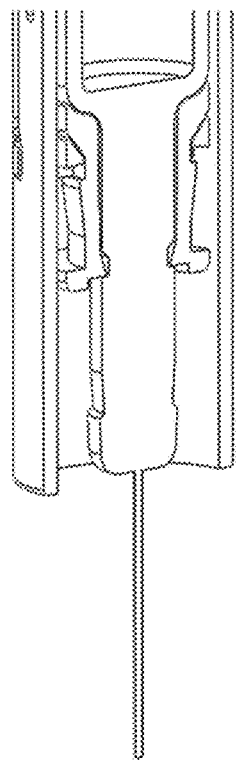

Turning to FIGS. 37A and B, at the top of the sloped ramp 114 of the lock collar 110 includes a flat surface 115. Once the lock ring 150 rides completely up the sloped ramp 114 it will relax back to its original shape with its bottom surface 154 resting on the flat surface 115 of the sloped ramp 114. Two protrusions 156 (one on each side) on the lock ring 150 are now mated with and match the outer dimensions of the syringe 160 barrel. They are also in vertical alignment with the device shield lockout arms 122.

Figure 38A:
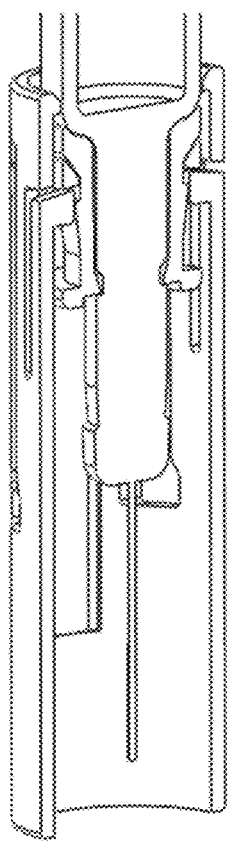
FIGS. 38A and B are cross sectional partial isometric views of the alternate lockout method embodiment after the needle has been fully removed from the injection site and the device is in the locked state.
Figure 38B:
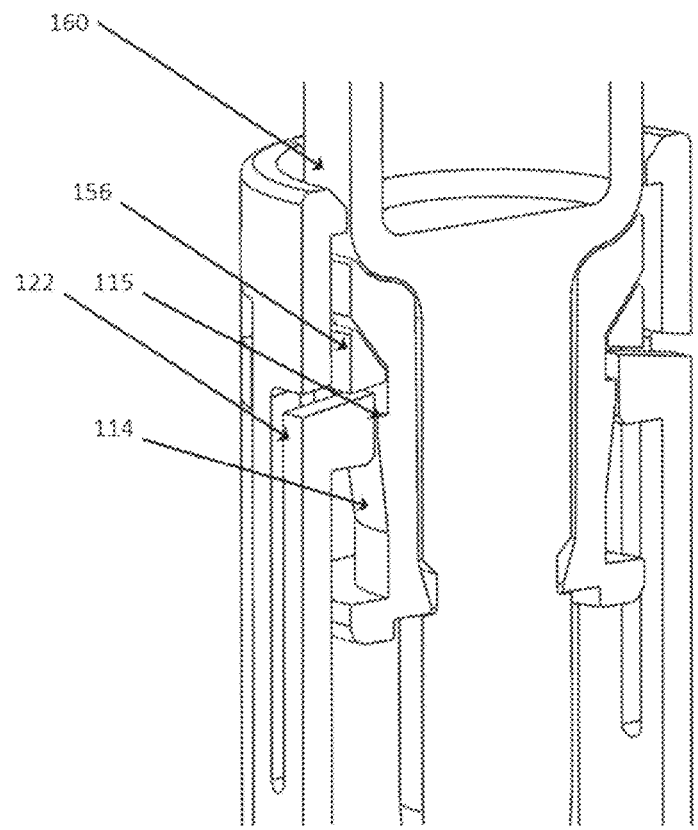

After the injection is complete and the syringe is pulled from the injection site, the device shield 120 will move distally back down the syringe 160 barrel as was described in the previous embodiment due to the elasticity and spring force generated by the flexible interconnect 130. To lockout the safety device, the device shield lockout arms 122, in a flexed beam state as the needle is being removed from the injection site, will transfer contact from the syringe 160 barrel to the lock ring protrusions 156, and, as shown in FIGS. 38A and B, then snap into place under the protrusions 156. Since, as shown in FIG. 32, the lock ring 150 is constrained vertically by the flat surface 115 of the lock collar sloped ramps 114 and the bottom surface of the lock collar lip 119, the shield 120 will be unable to move up or down relative to the syringe barrel 160, consequently locking the device and protecting the user from an accidental needle stick.

In the foregoing specification, the invention has been described with reference to specific embodiments thereof. It will, however, be evident that various modifications and changes may be made thereto without departing from the broader spirit and scope of the invention. For example, the reader is to understand that the specific ordering and combination of process actions shown in the process flow diagrams described herein is merely illustrative, unless otherwise stated, and the invention can be performed using different or additional process actions, or a different combination or ordering of process actions. As another example, each feature of one embodiment can be mixed and matched with other features shown in other embodiments. Features and processes known to those of ordinary skill may similarly be incorporated as desired. Additionally and obviously, features may be added or subtracted as desired. Accordingly, the invention is not to be restricted except in light of the attached claims and their equivalents.

What is claimed is:

1. A needle guard couplable to a ready-to-fill syringe comprising
    a lock collar couplable to a neck of a syringe,
    a lock ring assembled to the lock collar,
    a device shield, and
    a flexible member interconnecting the lock collar and the device shield, wherein the device shield is movable relative to the lock collar from a first configuration where the device shield is free to retract proximally to expose a syringe sharp to a second configuration where the device shield is fixed in a position covering the syringe sharp, wherein the device shield is caused to disengage from the first configuration as the device shield moves proximally enabling the device shield to move distally under the bias of the flexible member to the second configuration,
    wherein the device shield includes one or more lockout arms and the lock ring includes one or more protrusions, wherein the one or more lockout arms engage the one or more protrusions to retain the device shield in the second configuration.

2. The needle guard of claim 1 wherein the flexible member is configured to store energy as the device shield moves proximally relative to the lock collar and bias the device shield to move distally toward the second configuration.

3. The needle guard of claim 1 further comprising a rigid needle shield assembly releasably coupled to the neck of the syringe.

4. The needle guard of claim 3 wherein the needle shield assembly comprises a rigid needle shield component and a soft needle shield component received in the rigid need shield component.

5. The needle guard of claim 1 wherein the one or more lockout arms having a top surfaces abutting a bottom surface of the one or more protrusions.

6. The needle guard of claim 1 wherein the lock collar includes one or more lock collar tabs receivable in a recess in the neck of the syringe to retain the lock collar on the neck of the syringe.

7. The needle guard of claim 1 wherein the lock ring includes one or more tabs received in one or more channels in the device shield.

8. The needle guard of claim 7 wherein as the device shield moves in the proximal direction, the lock ring is moveable in the proximal direction from a first position adjacent the distal end of the lock collar to a second position adjacent the proximal end of the lock collar where axial movement of the lock ring is constrained.

9. The needle guard of claim 8 wherein the lock collar includes one or more ramps sloping outward in a proximal direction and a lip adjacent the proximal end of the lock collar, wherein the lock ring is constrained between the lip and a top surface of one or more ramps.

10. The needle guard of claim 1 wherein the lock ring is C-shaped.

11. A syringe assembly comprising
a syringe,
a needle extending from a syringe neck at a distal end of the syringe, and
a needle guard coupled to the syringe neck, the needle guard including a lock collar coupled to the syringe neck and a lock ring coupled to the lock collar, and
a device shield biased to move relative to the lock collar by a flexible member coupled to the device shield and the lock collar, wherein the needle guard having a first configuration where the device shield is movable proximally relative to the lock collar to expose a syringe sharp and a second configuration where the syringe sharp is fixedly covered by the device shield, and wherein the device shield is caused to disengage from the first configuration as the device shield moves proximally enabling the device shield to move distally under the bias of the flexible member to the second configuration,
wherein the device shield includes one or more lockout arms and the lock ring includes one or more protrusions, wherein the one or more lockout arms engage the one or more protrusions to retain the device shield in the second configuration.

12. The syringe assembly of claim 11 wherein the flexible member is configured to store energy as the device shield moves proximally relative to the lock collar and bias the device shield to move distally toward the second configuration.

13. The syringe assembly of claim 11 further comprising a rigid needle shield assembly releasably coupled to the neck of the syringe.

14. The syringe assembly of claim 13 wherein the needle shield assembly comprises a rigid needle shield component and a soft needle shield component received in the rigid need shield component.

15. The syringe assembly of claim 11 wherein the one or more lockout arms having a top surface abutting a bottom surface of the one or more protrusions.

16. The syringe assembly of claim 11 wherein the lock collar includes one or more lock collar tabs receivable in a recess in the syringe neck to retain the lock collar on the syringe neck.

17. The syringe assembly of claim 11 wherein the lock ring includes one or more tabs received in one or more channels in the device shield.

18. The syringe assembly of claim 17 wherein as the device shield moves in the proximal direction, the lock ring is moveable in the proximal direction from a first position adjacent the distal end of the lock collar to a second position adjacent the proximal end of the lock collar where axial movement of the lock ring is constrained.

19. The syringe assembly of claim 18 wherein the lock collar includes one or more ramps sloping outward in a proximal direction and a lip adjacent the proximal end of the lock collar, wherein the lock ring is constrained between the lip and a top surface of one or more ramps.

20. The syringe assembly of claim 11 wherein the lock ring is C-shaped.

* * * * *